United States Patent
Lubinski et al.

(10) Patent No.: US 10,792,020 B2
(45) Date of Patent: Oct. 6, 2020

(54) TAPERED GEOMETRY IN A COMPRESSIBLE CELL COLLECTION DEVICE

(71) Applicant: COVIDIEN LP, Mansfield, MA (US)

(72) Inventors: Alexander A. Lubinski, Rocklin, CA (US); Mark A. Maguire, Hillsborough, CA (US)

(73) Assignee: Covidien LP, Mansfield, MA (US)

( * ) Notice: Subject to any disclaimer, the term of this patent is extended or adjusted under 35 U.S.C. 154(b) by 333 days.

(21) Appl. No.: 14/856,743

(22) Filed: Sep. 17, 2015

(65) Prior Publication Data
US 2016/0081672 A1 Mar. 24, 2016

Related U.S. Application Data

(60) Provisional application No. 62/052,219, filed on Sep. 18, 2014.

(51) Int. Cl.
*A61B 10/02* (2006.01)

(52) U.S. Cl.
CPC ...... *A61B 10/02* (2013.01); *A61B 2010/0208* (2013.01)

(58) Field of Classification Search
None
See application file for complete search history.

(56) References Cited

U.S. PATENT DOCUMENTS

| | | |
|---|---|---|
| 2,701,559 A | 2/1955 | Cooper |
| 3,118,439 A | 1/1964 | Perrenoud |
| 3,608,549 A | 9/1971 | Merrill |
| 3,688,763 A | 9/1972 | Comarty |
| 3,706,311 A | 12/1972 | Kokx et al. |
| 3,877,464 A * | 4/1975 | Vermes ............ A61B 10/0291 600/572 |
| 4,077,409 A | 3/1978 | Murray et al. |
| 4,172,446 A * | 10/1979 | Bucalo ............... A61M 31/00 435/309.1 |
| 4,186,730 A * | 2/1980 | Bucalo ............... A61B 10/0045 435/309.1 |
| 4,239,040 A | 12/1980 | Hosoya et al. |
| 4,315,509 A * | 2/1982 | Smit .................. A61F 5/0076 417/474 |
| 4,481,952 A | 11/1984 | Pawelec |
| 4,735,214 A | 4/1988 | Berman |
| 4,883,465 A * | 11/1989 | Brennan ............. A61M 27/00 604/96.01 |
| 4,979,947 A | 12/1990 | Berman |

(Continued)

FOREIGN PATENT DOCUMENTS

| | | |
|---|---|---|
| CN | 2050741 | 1/1990 |
| FR | 2374048 | 7/1978 |

*Primary Examiner* — Sean P Dougherty
*Assistant Examiner* — Benjamin S Melhus
(74) *Attorney, Agent, or Firm* — Holland & Hart LLP

(57) ABSTRACT

Methods, apparatuses and systems for collecting cells from a body lumen are described. A system may include a cell collection device comprising an abrasive material configured to collect cells from the body lumen by scraping a surface of the body lumen. The cell collection device may have a first end with a first diametric dimension and a second end with a second diametric dimension, wherein the second diametric dimension is larger than the first diametric dimension.

12 Claims, 37 Drawing Sheets

(56) References Cited

U.S. PATENT DOCUMENTS

| | | | |
|---|---|---|---|
| 5,113,871 A | | 5/1992 | Viljanto et al. |
| 5,316,015 A | * | 5/1994 | Sinaiko .................. A61B 10/02 |
| | | | 600/582 |
| 5,370,656 A | * | 12/1994 | Shevel .................... A61F 13/36 |
| | | | 206/440 |
| 5,383,891 A | | 1/1995 | Walker |
| 5,411,022 A | * | 5/1995 | McCue .................... A61B 5/05 |
| | | | 600/361 |
| 5,453,078 A | | 9/1995 | Valentine et al. |
| 5,542,914 A | | 8/1996 | Van Iten |
| 5,738,100 A | | 4/1998 | Beal et al. |
| 7,294,346 B2 | | 11/2007 | Chalmers |
| 7,335,219 B1 | | 2/2008 | Ashby et al. |
| 8,517,961 B2 | | 8/2013 | Imran et al. |
| 8,603,132 B2 | | 12/2013 | Anwar |
| 8,722,066 B2 | | 5/2014 | Costa |
| 2011/0066175 A1 | | 3/2011 | Gross |
| 2011/0172557 A1 | * | 7/2011 | Lonky .................... A61B 10/02 |
| | | | 600/569 |
| 2012/0165796 A1 | * | 6/2012 | Ortiz ...................... A61B 1/041 |
| | | | 604/891.1 |
| 2012/0226189 A1 | | 9/2012 | Fitzgerald et al. |
| 2013/0338533 A1 | * | 12/2013 | Olsen ................ A61B 10/0291 |
| | | | 600/569 |

\* cited by examiner

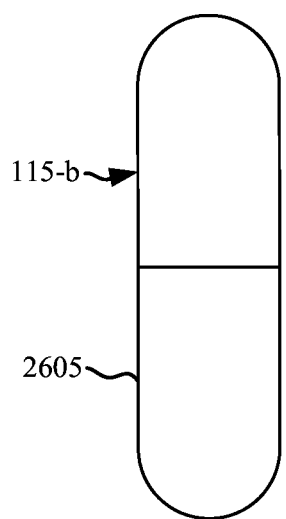
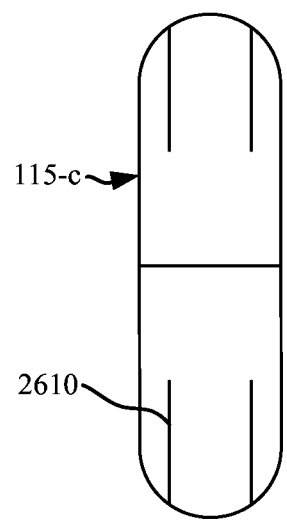
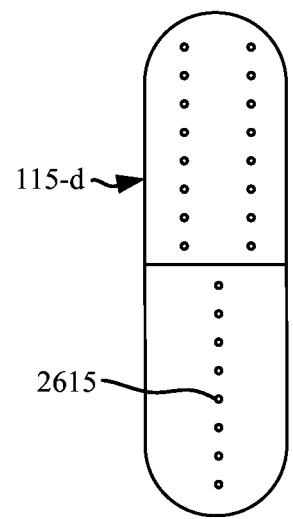
FIG. 26A     FIG. 26B     FIG. 26C
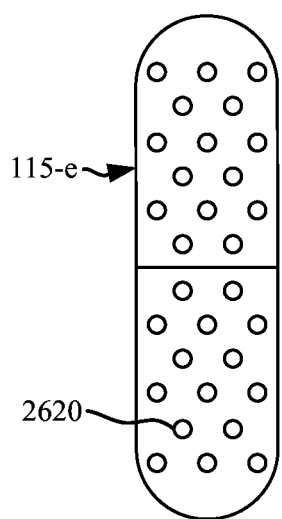
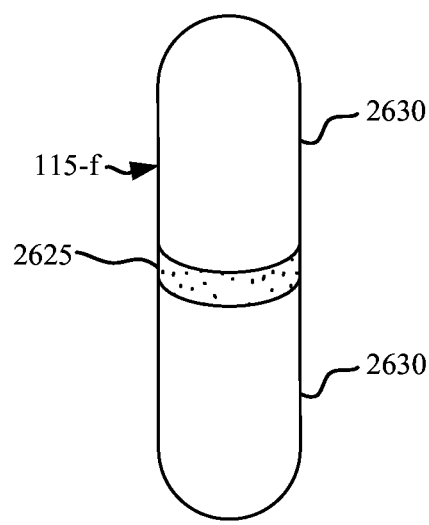
FIG. 26D     FIG. 26E

TAPERED GEOMETRY IN A COMPRESSIBLE CELL COLLECTION DEVICE

CROSS REFERENCE TO RELATED APPLICATION

The present application claims the benefit of and priority to U.S. Provisional Application Ser. No. 62/052,219, filed on Sep. 18, 2014, the entire contents of which are incorporated herein by reference.

BACKGROUND

To diagnose certain gastrointestinal diseases, an apparatus may be used to collect tissue cells from the gastrointestinal tract for analysis outside of the body. Typically, such an apparatus may include a material that is absorptive or abrasive for collecting the tissue cells. The material may be attached to a retrieval string so that it may be retrieved from the gastrointestinal tract or it may be allowed to naturally pass through the digestive system. Sometimes the material is compressed and encased within a capsule that is swallowed and naturally dissolves within the gastrointestinal tract.

However, conventional methods of collecting cells from the gastrointestinal tract may suffer from several deficiencies, which reduce the accuracy and reliability of the diagnoses, as well as increase the discomfort to the patient. For example, a typical cell collection material may be designed to collect cells from a body lumen with a relatively uniform size. As such, typical cell collection apparatuses may be incapable of adequately collecting cells from a body lumen with portions of varying size.

Accordingly, there may be a need for improved methods and devices to collect cells from the gastrointestinal tract of a patient that overcome some or all of the above deficiencies.

SUMMARY

The described features generally relate to one or more improved methods, systems, or devices for collecting cells from a body lumen. In general, an apparatus for collecting cells from a body lumen may include a cell collection device made from a sponge-like material that is compressed and encased within a swallowable capsule and attached to a retrieval string. The capsule may be swallowed or otherwise placed in the body lumen where it releases the cell collection device, allowing it to expand within the body lumen.

According to various embodiments, an apparatus for collecting cells from a body lumen may include a cell collection device comprising a plurality of distinct regions, each region including one or more material properties, wherein at least one material property of at least one distinct region differs from at least one material property of at least one other distinct region. The apparatus further includes a capsule configured to releasably retain the cell collection device. In some embodiments, at least one of the distinct regions of the cell collection device comprises a different material than at least one other distinct region. Additionally or alternatively, at least two of the distinct regions of the cell collection device comprise the same material, wherein at least one of the two distinct regions is mechanically or chemically altered to yield the at least one differing material property. The plurality of distinct regions may be joined together by a mechanical, chemical, or adhesive process.

The material properties of the cell collection device may include roughness, porosity, compressibility, absorbency, solubility, elasticity, lubricity, or malleability. In some embodiments, at least one of the distinct regions of the cell collection device is at least circumferentially encapsulated by one other distinct region. In such examples, the at least one encapsulated region may be more compressible than the encapsulating region. In other embodiments, the at least one encapsulated region may be less compressible than the encapsulating region and may include one or more elastic members such as a spring or stent. The at least one encapsulated region is completely encapsulated by the encapsulating region in some examples.

In certain aspects, at least one of the distinct regions of the cell collection device is substantially wedge-shaped. In such embodiments, the substantially wedge-shaped region may be more compressible than at least one other distinct region. The cell collection device is substantially spherically shaped in some embodiments. In yet other embodiments, the cell collection device is substantially cylindrically shaped. In such embodiments, at least one of the distinct regions of the substantially cylindrically shaped cell collection device is substantially cylindrically shaped and is adjacent to another distinct region that is substantially cylindrically shaped.

In some embodiments, at least one of the plurality of distinct regions of the cell collection device is configured to collect a different type of cell from the body lumen than at least one other distinct region. Additionally or alternatively, at least one of the plurality of distinct regions of the cell collection device may be configured to exert a different pressure against the inside of the body lumen than at least one other distinct region.

According to various embodiments, the cell collection device may further comprise a coating. The coating may include a lubricant, an analgesic, or a hydrophilic. The apparatus for collecting cells from a body lumen may further include a retrieval string coupled with the cell collection device. In some embodiments, the cell collection device is biodegradable.

According to various embodiments, an apparatus for collecting cells from a body lumen may include a cell collection device comprising an abrasive material configured to collect cells from the body lumen by scraping a surface of the body lumen. The cell collection device may have a first end with a first diametric dimension and a second end with a second diametric dimension, wherein the second diametric dimension is larger than the first diametric dimension. In some embodiments, the cell collection device includes a cavity extending from the second end towards the first end.

The cell collection device may be shaped substantially as a conical frustum. In such embodiments, the cell collection device may further include a cavity shaped substantially as a conical frustum. In other examples, the cell collection device is substantially conically shaped. In such examples, the cell collection device may further include a cavity that is substantially conically shaped. In yet other embodiments, the cell collection device may be shaped substantially as a paraboloid. Moreover, a paraboloid shaped cell collection device may further include a cavity that is substantially shaped as a paraboloid. In accordance with some embodiments, the cell collection device is substantially cylindrically shaped. In certain aspects, a substantially cylindrically shaped cell collection device may further include a plurality of fins.

The apparatus for collecting cells from a body lumen may further comprise a retrieval string coupled with the cell collection device. In such embodiments, the cell collection device may further include a cavity extending from the first end towards the second end, wherein the retrieval string extends through the first end of the cell collection device.

According to various embodiments, an apparatus for collecting cells from a body lumen may include a swallowable cell collection device comprising an abrasive and substantially non-absorbent material in a compressed configuration and configured to collect cells from the body lumen by scraping a surface of the body lumen. The apparatus may further include one or more expansion elements coupled with the cell collection device configured to expand the cell collection device from the compressed configuration. In certain embodiments, the one or more expansion elements are disposed within the cell collection device. For example, the one or more expansion elements may be disposed within a hollow cavity of the cell collection device. In such embodiments, the expansion element may include a stent. Additionally or alternatively, the one or more expansion elements may be coupled with an outside surface of the cell collection device. In such embodiments, the one or more expansion elements may include torsion springs or tension elements.

According to various embodiments, the one or more expansion elements comprise one or more springs. The one or more springs may include torsion springs, leaf springs, or helical springs. In some examples, the one or more expansion elements are configured to circumferentially expand the cell collection device.

In certain embodiments, the apparatus for collecting cells from a body lumen comprises two expansion elements arranged orthogonal to each other. In such embodiments, the two expansion members may include torsion springs. Moreover, the cell collection device may include four legs formed by arranging the abrasive and substantially non-absorbent material of the cell collection device about each of the two torsion springs. Alternatively, the apparatus for collecting cells from a body lumen may comprise three expansion elements arranged orthogonal to each other. In such examples, the expansion elements may include helical springs.

According to some embodiments, the cell collection device is substantially spherically shaped. Alternatively, the cell collection device may be substantially cylindrically shaped.

In certain embodiments, the one or more expansion elements comprise a heat activated material configured to expand the cell collection device once heated to an activation temperature. Additionally or alternatively, the expansion element may comprise a superelastic material. For example, nitinol may be used as the heat-activated material or as the superelastic material.

The apparatus for collecting cells from a body lumen may further include a dissolvable capsule configured to releasably retain the cell collection device in the compressed configuration. Additionally, the apparatus may further include a retrieval string coupled with the cell collection device.

According to various embodiments, an apparatus for collecting cells from a body lumen may include a plurality of swallowable cell collection devices comprising an abrasive material configured to collect cells from the body lumen by scraping a surface of the body lumen and a retrieval apparatus coupled with the plurality of swallowable cell collection devices. According to various embodiments, the swallowable cell collection devices are arranged in a spaced apart configuration. Additionally or alternatively, the plurality of swallowable cell collection devices may be arranged in a grouped configuration.

In certain aspects, the retrieval apparatus is configured to adjust a spatial relationship between at least one of the plurality of swallowable cell collection devices and at least one other of the plurality of swallowable cell collection devices within the body lumen. For example, the retrieval apparatus may be configured to spatially adjust the plurality of swallowable cell collection devices between a grouped configuration and a spaced apart configuration.

The retrieval apparatus may comprise one or more strings. Each of the swallowable cell collection devices may be coupled with an individual connector string that is coupled with a main retrieval string of the retrieval apparatus. In some embodiments, at least one connector string comprises a material with a different elasticity than at least one other connector string. Additionally or alternatively, the retrieval apparatus further comprises a junction that couples the main retrieval string to the individual connector strings, wherein the junction is configured to facilitate a spatial adjustment of at least one of the swallowable cell collection devices with respect to at least one other swallowable cell collection device.

According to various embodiments, the apparatus for collecting cells from a body lumen further comprises one or more dissolvable capsules configured to releasably retain the plurality of swallowable cell collection devices. In certain aspects, each of the plurality of swallowable cell collection devices is releasably retained in a separate dissolvable capsule. Alternatively, each of the plurality of swallowable cell collection devices may be releasably retained in a single dissolvable capsule.

A method of collecting cells from a body lumen is described according to various embodiments. The method may include providing a plurality of swallowable cell collection devices for collecting cells within the body lumen, wherein the plurality of swallowable cell collection devices comprise an abrasive material configured to collect cells from the body lumen by scraping a surface of the body lumen. The method may further include retrieving the plurality of swallowable cell collection devices from the body lumen with a retrieval apparatus coupled with the plurality of swallowable cell collection devices.

In some embodiments, retrieving the plurality of swallowable cell collection devices comprises adjusting a spatial relationship between at least one of the swallowable cell collection devices with respect to at least one other swallowable cell collection device. For example, adjusting a spatial relationship may comprise transitioning the plurality of swallowable cell collection devices between a grouped configuration and a spaced apart configuration. In certain aspects, a diametric dimension of the plurality of swallowable cell collection devices in the grouped configuration is greater than a diametric dimension of any of the swallowable cell collection devices individually. Moreover, in some embodiments, the plurality of swallowable cell collection devices are transitioned into a grouped configuration when the cell collection devices are retrieved past a portion of the body lumen where a diametric dimension of the body lumen exceeds the diametric dimension of any of the swallowable cell collection devices individually.

According to various embodiments, an apparatus for collecting cells from a body lumen may include a swallowable cell collection device including an abrasive and substantially non-absorbent material configured to collect cells from the body lumen by scraping a surface of the body lumen and a swallowable and dissolvable capsule including a plurality of scoring features configured to releasably retain the cell collection device. The plurality of scoring features of the cell collection device may be configured to mechanically weaken the capsule.

In some embodiments, the plurality of scoring features include one or more fenestrations. The plurality of scoring features may include one or more slits. Additionally or alternatively, the plurality of scoring features may include one or more indentations. In certain aspects, the plurality of scoring features are configured to control the orientation of the cell collection device with respect to the capsule when the cell collection device is released from the capsule. The apparatus for collecting cells from a body lumen further includes a retrieval string coupled with the cell collection device in certain examples.

A method of manufacturing an apparatus for collecting cells from a body lumen is described according to various embodiments. The method may include encapsulating a swallowable cell collection device comprising an abrasive and substantially non-absorbent material within a swallowable and dissolvable capsule and mechanically weakening the capsule with a plurality of scoring features. In certain examples, the plurality of scoring features comprises one or more fenestrations. The plurality of scoring features may comprise one or more slits in some embodiments. Additionally or alternatively, the plurality of scoring features may include one or more indentations. According to certain aspects, the plurality of scoring features are configured to control the orientation of the cell collection device with respect to the capsule when the cell collection device is released from the capsule.

According to various embodiments, an apparatus for collecting cells from a body lumen may include a cell collection device comprising an abrasive material configured to collect cells from a surface of a body lumen. The apparatus may further include a capsule configured to releasably retain the cell collection device in a compressed configuration until the activation of one or more active triggers that control the release of the cell collection device from the capsule.

In some embodiments, the one or more active triggers comprise applying an electrical current to the capsule. Moreover, the apparatus may further include a retrieval string coupled with the cell collection device. In such embodiments, the one or more active triggers may comprise applying an electrical current to the capsule via the retrieval string. In certain aspects, the one or more active triggers comprises applying a chemical solution to the capsule. In such embodiments, the chemical solution may be swallowed.

According to various embodiments, the one or more active triggers may include heating the capsule. Heating the capsule my include applying an electrical current to the capsule. Additionally or alternatively, heating the capsule may include swallowing a liquid that heats the capsule. In some embodiments, the one or more active triggers includes applying an electromagnetic signal to the capsule via a power source external to the body lumen.

The capsule may comprise one or more pH-sensitive polymers in some embodiments. Accordingly, the one or more pH-sensitive polymers may be configured to dissolve in the presence of an acidic liquid. In some embodiments, the capsule may include a combination of dissimilar metallic materials.

According to various embodiments, a method of collecting cells from a body lumen may include providing a capsule configured to releasably retain a cell collection device within the body lumen, wherein the cell collection device is configured to collect cells from a surface of the body lumen. The method may further include activating one or more active triggers that control the release of the cell collection device from the capsule.

In some embodiments, activating the one or more active triggers may comprise applying an electrical current to the capsule via a retrieval string. Activating the one or more triggers may include applying an electromagnetic signal to the capsule via a power source external to the body lumen. Additionally or alternatively, activating the one or more active triggers may comprise applying a chemical solution to the capsule. In yet other embodiments, activating the one or more active triggers may include heating the capsule. In such embodiments, heating the capsule may include applying an electrical current to the capsule. Moreover, heating the capsule may include swallowing a liquid that heats the capsule.

Certain embodiments of the present disclosure may include some, all, or none of the above advantages or features. One or more other technical advantages or features may be readily apparent to those skilled in the art from the figures, descriptions, and claims included herein. Moreover, while specific advantages or features have been enumerated above, various embodiments may include all, some, or none of the enumerated advantages or features.

Further scope of the applicability of the described methods and apparatuses will become apparent from the following detailed description, claims, and drawings. The detailed description and specific examples are given by way of illustration only, since various changes and modifications within the spirit and scope of the description will become apparent to those skilled in the art.

BRIEF DESCRIPTION OF THE DRAWINGS

A further understanding of the nature and advantages of the embodiments may be realized by reference to the following drawings. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

FIG. 26A is an illustration of a capsule of a cell collection apparatus in accordance with various embodiments;

FIG. 26B is an illustration of a capsule of a cell collection apparatus in accordance with various embodiments;

FIG. 26C is an illustration of a capsule of a cell collection apparatus in accordance with various embodiments;

FIG. 26D is an illustration of a capsule of a cell collection apparatus in accordance with various embodiments;

FIG. 26E is an illustration of a capsule of a cell collection apparatus in accordance with various embodiments;

DETAILED DESCRIPTION

Figure 1A:
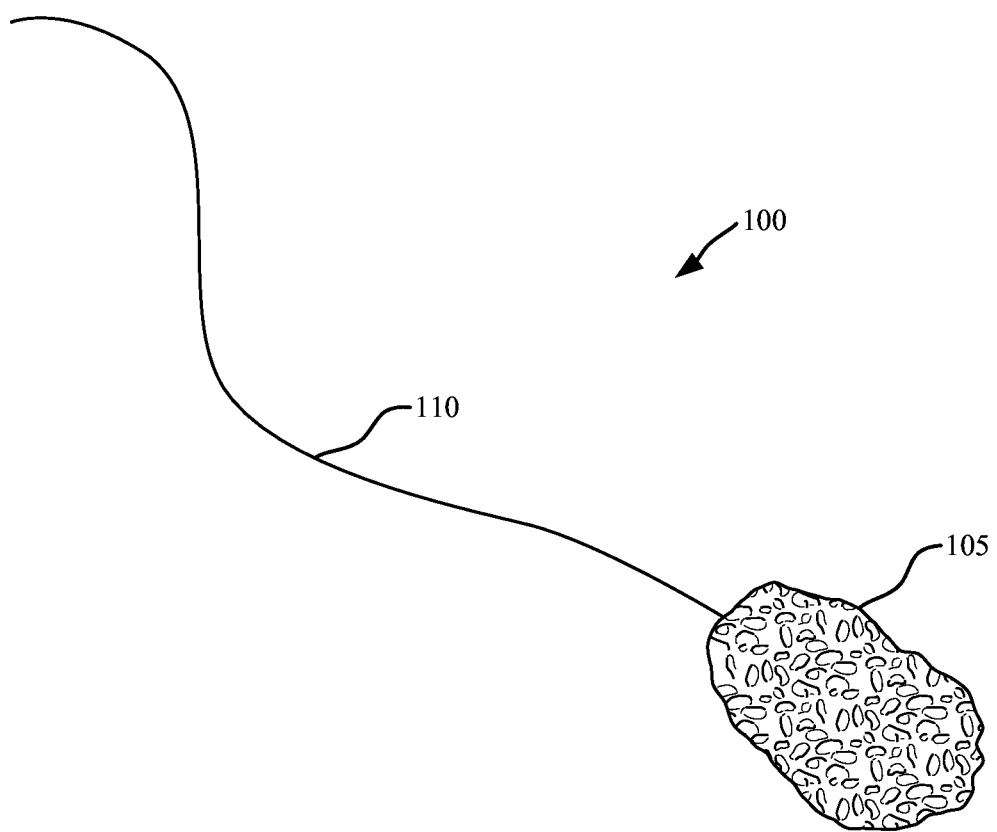
FIG. 1A is an illustration of a cell collection apparatus in accordance with various embodiments.

Methods, systems, and devices are described for collecting cells from a body lumen of a patient. Systems may include a swallowable cell collection device that may be retrieved from the stomach of a patient back through the mouth of the patient with a retrieval string. The cell collection device may include a sponge-like material that collects cells from the body lumen by scraping a surface of the body lumen as it is being retrieved. To increase the swallowability of the cell collection device, it may be compressed and encased within a swallowable and dissolvable capsule. Once the capsule is within the body lumen, it may dissolve or otherwise release the cell collection device from its compressed state, allowing the cell collection device to expand within the body lumen.

In some embodiments of the present invention, the cell collection device may include a plurality of distinct regions with different material properties. The different material properties of the distinct regions may be a result of mechanical or chemical processing, or the distinct regions may include different materials entirely with different material properties. The material properties and shapes of the distinct regions may be tailored to facilitate the collection of cells within body lumens of varying sizes. The cell collection device may also be shaped with a taper or other geometric feature that results in one end of the cell collection device having a larger diametric dimension than the other end. For example the cell collection device may be shaped as a cone, conical frustum, paraboloid, or any other tapered geometry. The cell collection device may also be cylindrically-shaped and include fins or other tapered geometric features. In some embodiments, the cell collection device may include a cavity or other hollowed portion that reduces the volume of cell collection device material.

According to some embodiments, the cell collection device may include one or more expansion elements configured to expand the cell collection device from a compressed configuration. The expansion elements may be positioned within the cell collection device or may be arranged on an outside surface of the cell collection device. The expansion elements may be springs, stents, or any other member capable of storing elastic potential energy to provide a force to assist in the expansion of the cell collection device.

In various embodiments, multiple cell collection devices may be retrieved simultaneously to collect cells from a body lumen. The multiple cell collection devices may be coupled with a retrieval means, such as a string, that is configured to retrieve the multiple cell collection devices from the body lumen. The retrieval means may be configured to adjust a spatial relationship between two or more of the cell collection devices within the body lumen. For example, the multiple cell collection devices may be transitioned between a grouped configuration, such as a bouquet, and a spaced apart configuration while being retrieved from the body lumen.

Additionally, the capsule that encases the cell collection device may include one or more features that facilitate controlling the release of the cell collection device from the capsule. In some embodiments, the capsule may include features that mechanically weaken the capsule in certain regions, such as slits, fenestrations, perforations, indentations, or any other similar feature. In yet other embodiments, the capsule may be configured to dissolve or otherwise release the cell collection device upon the activation of an active trigger. An active trigger may include applying an electric current, a chemical solution, or heat to the capsule. The active trigger may be applied directly to the capsule, such as via the retrieval means, or may be applied indirectly through an electromagnetic field or any other indirect means.

With reference to FIG. 1A, a general system 100 for collecting cells from a body lumen is shown in accordance with various embodiments. The system 100 may be used to collect cells from a body lumen of the upper gastrointestinal tract, such as the stomach and esophagus, for example. However, it may be appreciated that system 100 may be used to collect cells from a variety of body lumens, including any portion of the small intestine and large intestine. System 100 may include a cell collection device 105 that is tied, adhered, or otherwise coupled with a retrieval string 110. In some embodiments, retrieval string 110 is made from surgical suture material. However, it may be appreciated that a variety of natural or synthetic materials may be used, including metals and natural and synthetically-derived polymers. Moreover, in some embodiments, retrieval string 110 is made from a biodegradable material such that it will naturally dissolve within the body lumen over time in case the retrieval string 110 cannot be retrieved from the body lumen. Retrieval string 110 may be coated or otherwise treated to reduce the friction between string 110 and the throat of the patient, making string 110 easier to swallow and withdraw.

In general, collection device 105 is configured to collect cells from a body lumen by removing tissue or other cells from a surface of the body lumen. Accordingly, cell collection device 105 may be made from an abrasive material that collects cells by scraping, rubbing, or otherwise abrading a surface of the body lumen as it is being withdrawn by the retrieval string 110. In some embodiments, cell collection device 105 is made from an abrasive sponge-like material, such as reticulated polyurethane or polyester. Polyurethanes may include those made with polyester, polyether, polycaprolactone and other polyols. Additionally, polyurethane foams could be made from a variety of diisocyanates (MDI, TODI, PPDI or other) and chain extenders. One particular embodiment involves a polyurethane composed of polycaprolactone and TODI. It is envisioned that abrasive foams could also be made from other synthetic or natural polymers, either in the form of reticulated, open cell, or closed cell foams where the outer cells are open. Alternatively, a metallic mesh may be used to form cell collection device 105. In addition to being abrasive, cell collection device 105 is made from a substantially non-absorbent material in some embodiments. A substantially non-absorbent material is one where the fibers of the material do not absorb liquid and swell. For example, reticulated polyurethane, reticulated polyester, or metallic wire may be considered substantially non-absorbent. In contrast, materials like cotton may be considered absorbent due to the tendency of these materials to absorb liquid and swell.

In some embodiments, the material of cell collection device 105 is biodegradable such that it will naturally dissolve within the body lumen over time in case the cell collection device 105 cannot be retrieved by the retrieval string 110. Polylactic acid (PLA), polyglycolic acid (PGA), polylactic-co-glycolic acid (PLGA), and polycaprolactone (PCL) are examples of suitable synthetic biodegradable materials from which cell collection device 105 may be made. Scaffolds may also be used and constructed from natural materials. Naturally occurring materials such as polysaccharidic materials like cellulose, chitosan or glycosaminoglycans could also form the basis of suitable biodegradable materials. Degradation mechanisms for these materials are relatively similar, but may exhibit respectively faster or slower rates of degradation compared depending on formulations and combinations. In some examples, metallic materials such as magnesium and zinc may be used to make degradable vascular stents, and therefore could be suitable materials for making a degradable cell collection device 105.

As described in greater detail below, cell collection device 105 may include one or more features that enhance its ability to collect cells from a body lumen with portions of varying diameter, facilitate the collection of a variety of cell types with a single device, and allow the cell collection device 105 to perform functions other than and in addition to collecting cells. Additionally, in accordance with various embodiments, features of cell collection device 105 may increase the swallowability of the device. For example, the cell collection device 105 may include features that allow it to be highly compressed while maintaining sufficient expansion characteristics, or may allow the cell collection device 105 to maintain sufficient cell collection properties while requiring less material to be used. As described with reference to FIGS. 3-9, cell collection device 105 may include a plurality of distinct regions with differing material properties. In some embodiments, cell collection device 105 may be tapered or include one or more geometric features such that one end of the cell collection device 105 has a larger diametric dimension than the other end, as described in connection with FIGS. 10-14. In yet other embodiments, described with reference to FIGS. 15-21, cell collection device 105 may include one or more expansion elements configured to expand the cell collection device from a compressed configuration. Moreover, according to various embodiments described in connection with FIGS. 22-25, multiple cell collection devices 105 may be used simultaneously to collect cells from a body lumen.

Figure 1B:
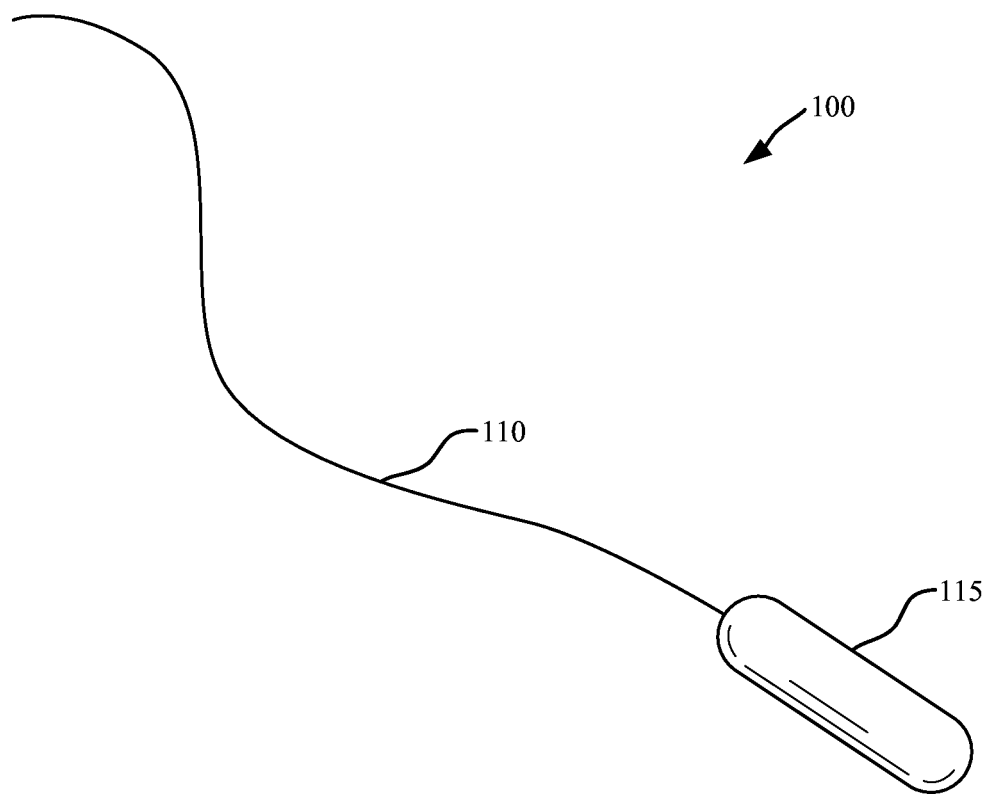
FIG. 1B is an illustration of a cell collection apparatus in accordance with various embodiments.

Turning to FIG. 1B, a system 100 for collecting cells from a body lumen is shown including a capsule 115. In general, capsule 115 is configured to encase a cell collection device, such as cell collection device 105, and deliver it to the inside of the body lumen from which cells or other tissue are to be collected. In some embodiments, capsule 115 is swallowable and delivers cell collection device 105 to the stomach of the patient. However, capsule 115 may be placed within the target body lumen using any conventional means such as surgical, or endoscopic. Once capsule 115 is placed within the body lumen, it may dissolve or otherwise release cell collection device 105, allowing cell collection device 105 to expand from a compressed configuration. Capsule 115 may be made from one or more synthetic materials or natural materials such as animal proteins (gelatin) or plant polysaccharides (starch or cellulose). As described in greater detail below, capsule 115 may include one or more features that allow the timing and manner of the release of cell collection device 105 to be controlled. For example, capsule 115 may include one or more features that mechanically weaken the walls of capsule 115, as described with reference to FIGS. 26-27. According to some embodiments, described in detail in connection with FIGS. 28-31, the release of cell collection device 105 from capsule 115 may be controlled by activating one or more active triggers.

Figure 2A:
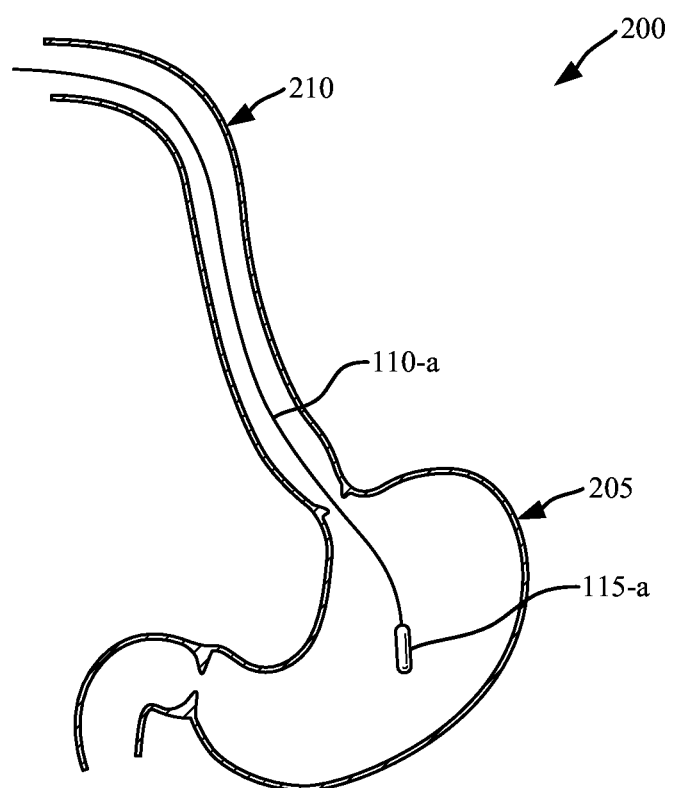
FIG. 2A is an illustration of a cell collection apparatus within the upper gastrointestinal tract of a human in accordance with various embodiments.

With reference to FIG. 2A, a general system 200 for collecting cells from the gastrointestinal tract of a patient is shown in accordance with various embodiments. System 200 may be an example of system 100 described in relation to FIG. 1. System 200 includes a capsule 115-a that is shown positioned within a stomach 205 of a patient. Capsule 115-a may have been swallowed or otherwise placed within stomach 205. System 200 may also include a retrieval string 110-a extending from capsule 115-a, out of stomach 205, and up through esophagus 210 of the patient. Although not shown, retrieval string 110-a extends all the way up through the mouth of the patient such that a physician or other user may grab the free end of retrieval string 110-a.

Figure 2B:
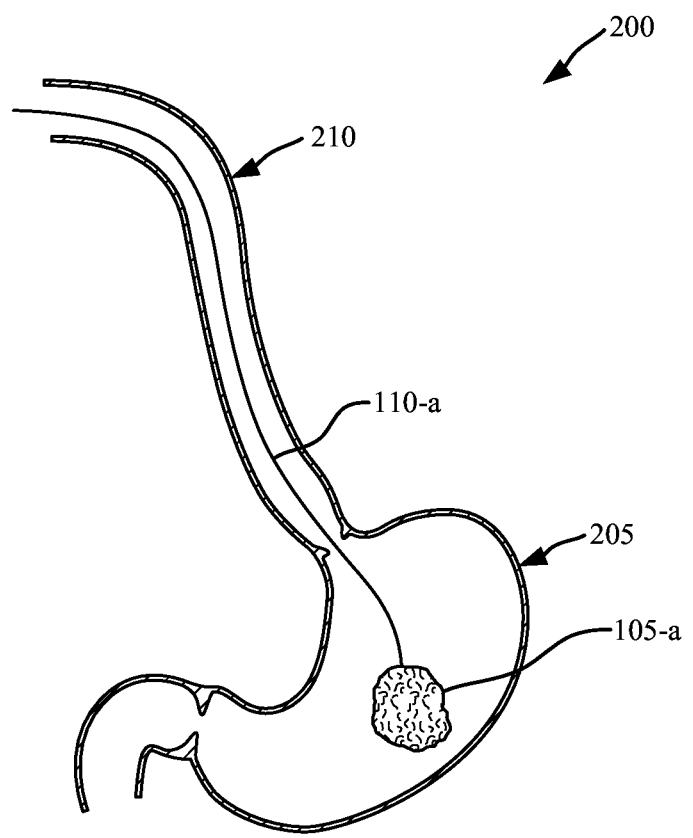
FIG. 2B is an illustration of a cell collection apparatus within the upper gastrointestinal tract of a human in accordance with various embodiments.

FIG. 2B illustrates system 200 with cell collection device 105-a released from capsule 115-a within stomach 205 of the patient. Cell collection device 105-a may be an example of cell collection device 105 described in connection with FIG. 1. In some embodiments, capsule 115-a may naturally dissolve and release cell collection device 105-a from a compressed configuration due to the temperature, acidity, and aqueous environment of the gastric fluids within stomach 205. Alternatively, as described in detail with reference to FIGS. 28-31, capsule 115-a may dissolve or otherwise release cell collection device 105-a from a compressed configuration upon the activation of an active trigger. Once cell collection device 105-a is released from capsule 115-a, it may expand to an expanded configuration. An expanded configuration may be larger along at least one dimension than the compressed configuration within the capsule 115-a. In some embodiments, cell collection device 105-a may expand to an expanded configuration naturally due the elasticity or other natural expansion characteristics of the cell collection device material. Alternatively, or additionally, cell collection device 105-a may include one or more expansion members configured to expand cell collection device 105-a to an expanded configuration. Examples of expansion members in accordance with various embodiments are described in detail in connection with FIGS. 15-21.

Figure 2C:
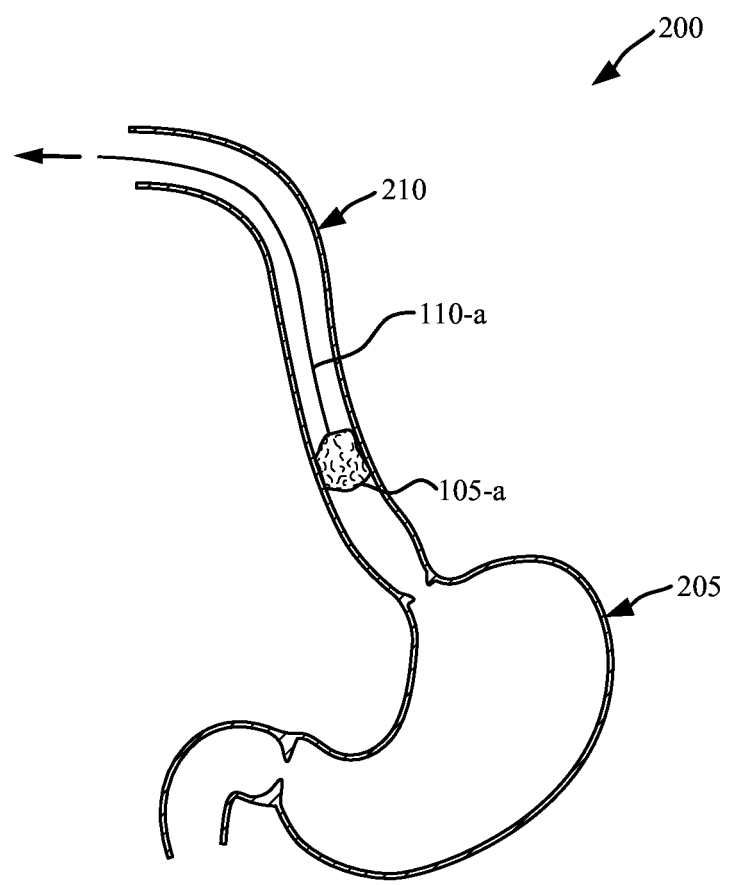
FIG. 2C is an illustration of a cell collection apparatus being withdrawn from the upper gastrointestinal tract of a human in accordance with various embodiments.

With reference to FIG. 2C, cell collection device 105-a is shown being withdrawn up through esophagus 210 of the patient by the retrieval string 110-a. As described above, cell collection device 105-a may collect cells from stomach 205 and esophagus 210 by scraping a surface of the walls of these body lumens. In its relaxed, collapsed state, the walls of esophagus 210 generally do not form a perfect, cylindrical tube. Rather, the walls of esophagus 210 undulate into a plurality of folds. Accordingly, as cell collection device 105-a is being retrieved, it may unfold the walls of the esophagus 210 to form a substantially cylindrical-shaped portion proximal to the cell collection device 105-a. Depending on the diameter of esophagus 210 at a given location, and the diameter and expansion characteristics of cell collection device 105-a in its expanded configuration, cell collection device 105-a may contact the full circumferential surface of esophagus 210, or it may only contact a partially circumferential portion of the esophageal wall.

To increase the accuracy and reliability of a cell collection procedure, it may be desirable for cell collection device 105-a to contact substantially the full circumferential surface of the walls of esophagus 210. Accordingly, the size, shape, and/or expansion characteristics of cell collection device 105-a may be configured to unfold the walls of esophagus 210 and substantially contact and collect cells from the full circumferential surface of the esophageal walls. As described in greater detail in relation to FIGS. 10-14, the shape of cell collection device 105-a may be configured to provide a sufficient outward force on the walls of esophagus 210 to unfold the walls such that cell collection device 105-a may contact the full circumferential surface of esophagus 210. Additionally, or alternatively, one or more expansion elements, described in connection with FIGS. 15-21, may be coupled with cell collection device 105-a to provide a sufficient outward force to unfold the walls of esophagus 210.

Figure 2D:
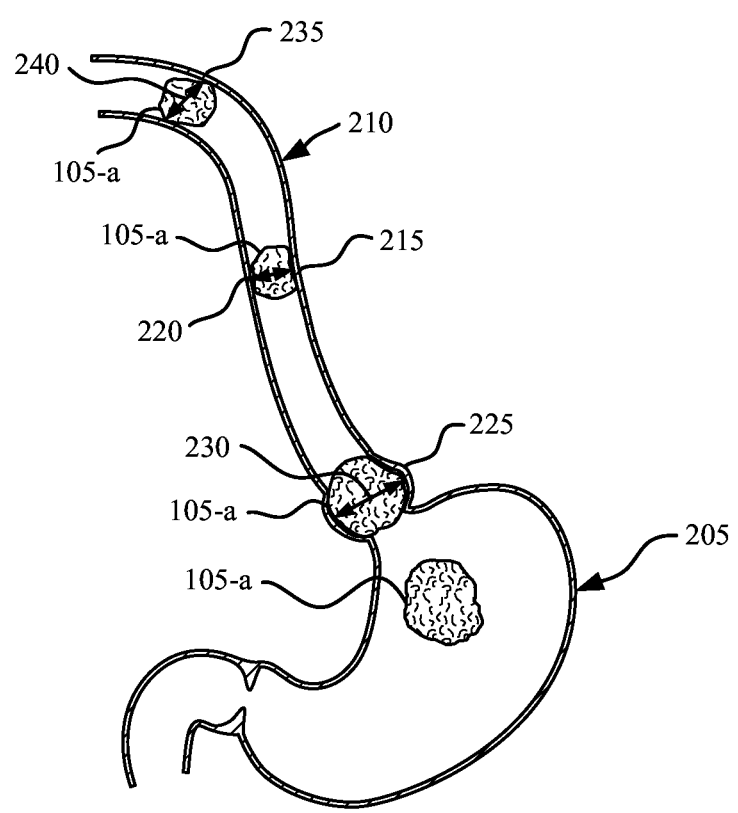
FIG. 2D is an illustration of a cell collection apparatus at various locations within the upper gastrointestinal tract of a human in accordance with various embodiments.

As shown with reference to FIG. 2D, the upper gastrointestinal tract may include multiple sections with varying sizes and shapes. Cell collection device 105-a is shown at various locations within the upper gastrointestinal tract to illustrate the expansion and compression capabilities of cell collection device 105-*a* is it is being withdrawn up through esophagus 210. The various portions of esophagus 210 with differing size may be due to natural variations in the esophageal anatomy, may be the result of a hernia or other injury, or may be caused by a temporary event such as the patient shifting or belching. Referring to FIG. 2D, esophagus 210 may include a portion 215 with a diameter 220. Diameter 220 may represent the average diameter of esophagus 210 of an average adult patient. In certain instances, a patient may have an enlarged portion 225 near the gastro-esophageal junction with a diameter 230 that is larger than the diameter 220. Enlarged portion 225 may represent a portion of the stomach 205 that has herniated upward, such as in the case of a sliding hiatal hernia. Alternatively, enlarged portion 225 may be due to a natural variation or a temporary event. Additionally, there may be another portion 235 along esophagus 210 proximal to the patient's throat with a diameter 240 that is smaller than the diameter 230 of enlarged portion 225. Diameter 240 may be larger, smaller, or substantially the same size as the average diameter 220.

It may be desirable to collect cells from all of the various portions 215, 225, and 235 along the stomach 205 and esophagus 210 with a single cell collection device 105-*a*. Accordingly, the shape and/or size of cell collection device 105-*a* may be configured to adapt to accommodate the various sizes 220, 230, and 240 of the stomach 205 and esophagus 210 while being withdrawn. For example, as described in connection with FIGS. 3-9, cell collection device 105-*a* may include multiple distinct regions with varying material properties. The varying material properties of these distinct regions may allow cell collection device 105-*a* to collect cells from multiple portions of esophagus 210 with varying sizes by expanding and compressing to match the local size of esophagus 210 as it is being retrieved. In some embodiments, the geometry of cell collection device 105-*a* may be configured to facilitate the collection of cells from larger portions of the esophagus 210, such as portion 225, while also allowing compression of the cell collection device 105-*a* into smaller portions, such as portion 235. Exemplary embodiments describing the geometry of such cell collection devices 105-*a* are described in connection with FIGS. 10-14.

Additionally or alternatively, as described with reference to FIGS. 15-21, cell collection device 105-*a* may include one or more expansion elements that facilitate the expansion of cell collection device 105-*a* to a sufficient diameter to collect cells from larger portions of the stomach 205 and esophagus 210, such as portion 225. In yet other embodiments, multiple cell collection devices 105-*a* may be retrieved simultaneously, allowing the collection of cells from multiple portions of stomach 205 and esophagus 210 with varying sizes. As described in greater detail with reference to FIGS. 22-25, multiple cell collection devices 105-*a* may be gathered into a group configuration to collect cells from larger portions, such as portion 225, and then may be transitioned into a spaced apart configuration to gather cells from smaller portions, such as portion 235.

As mentioned with reference to FIGS. 1-2, a cell collection device 105 may include multiple distinct regions with differing material properties. Such a cell collection device 105 may allow for the different regions to be optimized or configured for different purposes. For example, certain regions of a cell collection device 105 may be configured for collecting cells while other regions are configured for optimal expansion or compression. In other embodiments, some regions may be configured to collect a certain cell type or tissue layer, while others are configured to collect a different type of cell or tissue layer. Additionally, or alternatively, some regions may be configured for other purposes besides collecting cells, such as applying a lubricant, analgesic, or antibiotic to certain regions of the body lumen. The distinct regions may, in some examples, be made from different materials. In such examples, the distinct regions may be joined together by any appropriate mechanical, chemical, or adhesive process. Examples of mechanical joining processes include sewing, stapling, crimping, hooking, or any other envisioned mechanical method. Examples of chemical and adhesive processes include the use of functional groups to facilitate non-covalent and covalent bonding, and glues or other adhesives. Embodiments also may include over-molding techniques, wherein one part of the foam is fabricated and then the second part of the foam is fabricated, with the first part of the foam being incorporated within the second part. This could lead to mechanical and chemical bonding/interlocking networks. In other embodiments, the distinct regions are all made from the same material, but at least one material property has been altered in at least one of the regions. A material property of a distinct region may be altered by any suitable mechanical or chemical process. For example, a suitable mechanical or chemical process may include mechanical fenestration, cyclic loading conditioning, chemical etching, or the addition of chemical solvents, plasticizers or detergents.

Figure 3A:
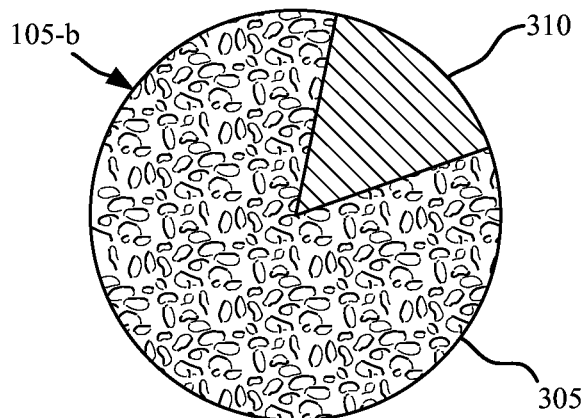
FIG. 3A is an illustration of a cell collection apparatus with multiple distinct regions in an expanded configuration in accordance with various embodiments.

Turning to FIG. 3A, a cross sectional view of a cell collection device 105-*b* with a plurality of distinct regions is shown in accordance with various embodiments. Cell collection device 105-*b* may be an example of a cell collection device 105 described in connection with any of FIGS. 1-2. Cell collection device 105-*b* may be shaped as a cylinder, sphere, or any other geometry with a substantially circular cross section as shown in FIG. 3A. Cell collection device 105-*b* may include a first region 305 and second region 310. In some embodiments, region 310 may be substantially wedge-shaped. As only a cross section of cell collection device 105-*b* is shown in FIG. 3A, it may be appreciated that wedge-shaped portion 310 may extend along the entire length or width of cell collection device 105-*b*, forming a three-dimensional wedge-shaped extrusion.

Each distinct region 305, 310 may include one or more material properties. Examples of material properties include compressibility, elasticity, roughness, solubility, malleability, absorbency, lubricity, and porosity. In accordance with various embodiments, at least one material property of one distinct region is different than at least one material property of at least one other distinct region. For example, with reference to FIG. 3A, the compressibility of region 305 may be different than the compressibility of region 310, while the roughness and porosity may be the same between the two regions. In another example, the roughness may differ between regions 305, 310, while the compressibility and porosity are the same between the regions. In yet another example, all of the material properties may differ between the two regions 305, 310.

Figure 3B:
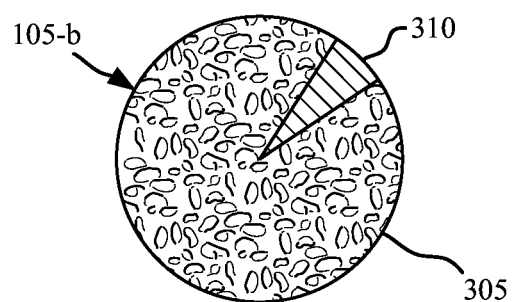
FIG. 3B is an illustration of a cell collection apparatus with multiple distinct regions in a compressed configuration in accordance with various embodiments.

As mentioned above, distinct regions 305, 310 may be configured or optimized for certain purposes that differ from region to region. For example, region 305 may be made from material A and region 310 may be made from material B. Material A may be optimized for cell collection but may have inadequate expansion or compression characteristics, while material B may be optimized for compression or expansion but may have inadequate cell collection characteristics. Accordingly, if cell collection device 105-*b* is being withdrawn through a portion of the esophagus 210 that requires the cell collection device 105-*b* to be circumferentially compressed, region 310 may compress more than region 305, resulting in a compressed configuration as shown in FIG. 3B. In accordance with the present example, cell collection device 105-b may exhibit superior expansion or compression capabilities (due to region 310), while also maintaining sufficient cell collection characteristics (due to region 305).

Figure 4A:
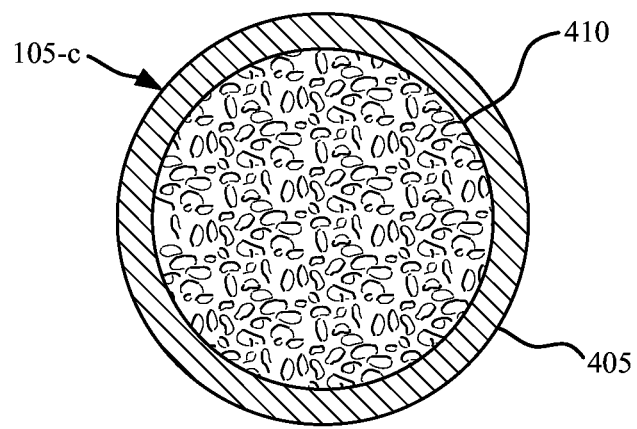
FIG. 4A is an illustration of a cell collection apparatus with multiple distinct regions in an expanded configuration in accordance with various embodiments.

With reference to FIG. 4A, a cross sectional view of a cell collection device 105-c with a plurality of distinct regions is shown in accordance with various embodiments. Cell collection device 105-c may be an example of a cell collection device 105 described in connection with any of FIGS. 1-3. Cell collection device 105-c may include an outer distinct region 405 that at least circumferentially encapsulates or surrounds an inner distinct region 410. For example, if cell collection device 105-c is substantially cylindrically-shaped, outer region 405 may form a ring of material and may only circumferentially surround inner region 410. In other embodiments, where cell collection device 105-c is substantially spherically-shaped, region 405 may form a spherical shell of material and may completely encapsulate or surround inner portion 410.

Figure 4B:
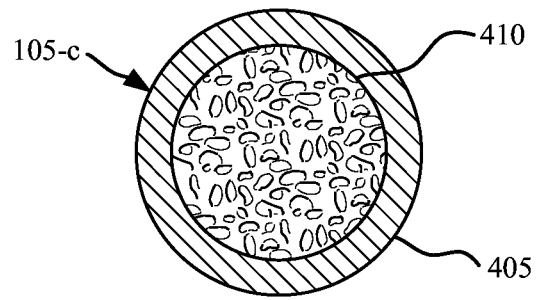
FIG. 4B is an illustration of a cell collection apparatus with multiple distinct regions in a compressed configuration in accordance with various embodiments.
Figure 5:
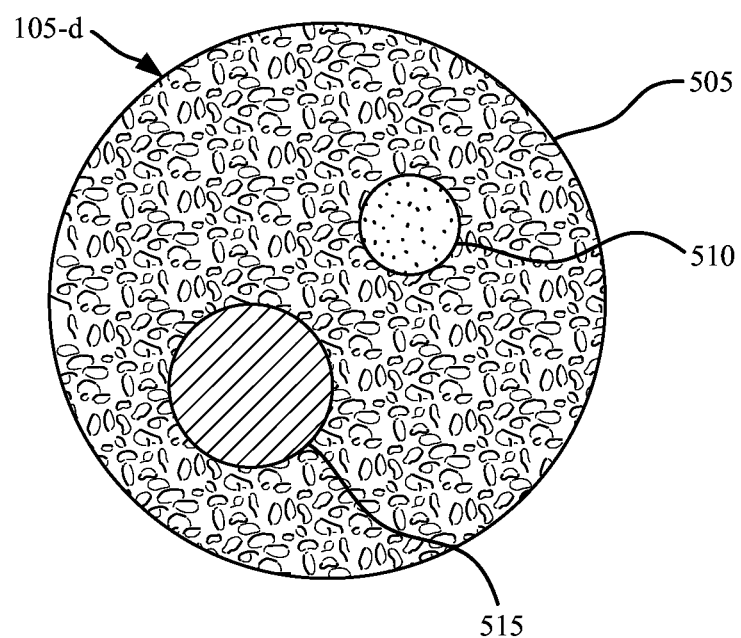
FIG. 5 is an illustration of a cell collection apparatus with multiple distinct regions in accordance with various embodiments.

As with cell collection device 105-b of FIG. 3, the distinct regions 405, 410 of cell collection device 105-c may have at least one material property that differs between the two regions. For example, the compressibility of region 410 may be greater than the compressibility of region 405. Accordingly, as shown in FIG. 4B, region 410 may compress more than region 405 when cell collection device 105-c is subject to circumferential compression forces when being withdrawn from an esophagus 210. In alternative examples, the internal region 410 may be less compressible than the outer region 405. In such examples, region 410 my include an elastic member, such as a spring or stent that provides an outward expansion force on the external region 405. Additionally, the cell collection characteristics of region 405 may be different than the cell collection characteristics of region 410. For example, the roughness of region 405 may be greater than the roughness of region 410. In other embodiments, region 410 may be hygroscopic whereas region 405 may be substantially non-absorbent and configured primarily for cell collection. Accordingly, region 410 may easily absorb liquid and swell, expanding cell collection device 105-c, where region 405 is configured to remove cells from the surface of the body lumen by scraping the body lumen surface.

It may be appreciated that any number of distinct region combinations may be formed to create a cell collection device 105 with certain cell collection, compression, or expansion characteristics as may be desired for a particular application. Although only two distinct regions are shown in FIGS. 3-4, it may be appreciated that any number of distinct regions may be used in the same cell collection device 105. For example, as shown in the cross sectional view of FIG. 5, a cell collection device 105-d may include three distinct regions 505, 510, and 515. Cell collection device 105-d may be an example of any cell collection device 105 described in connection with any of FIGS. 1-4. Inner regions 510 and 515 may be either circumferentially or spherically surrounded by outer region 505, depending on whether cell collection device 105-d is substantially cylindrically or spherically shaped. Regions 505, 510, and 515 may be made from different materials. In other embodiments, all of the regions 505, 510, 515 may be made from the same material where at least one material property of at least one of the regions has been altered by a mechanical or chemical process.

Figure 6:
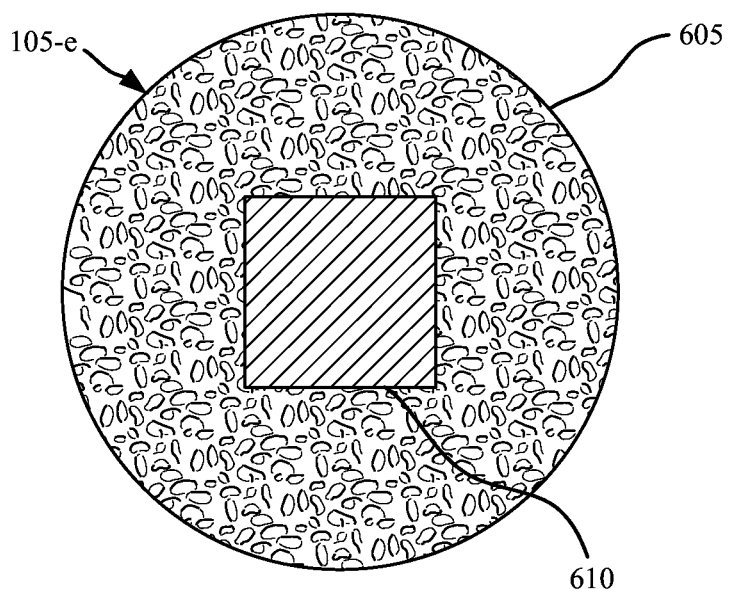
FIG. 6 is an illustration of a cell collection apparatus with multiple distinct regions in accordance with various embodiments.

Turning to FIG. 6, a cross sectional view of cell collection device 105-e with multiple distinct regions is shown in accordance with various embodiments. Cell collection device 105-e may be an example of any cell collection device 105 described in connection with any of FIGS. 1-5. As shown in FIG. 6, cell collection device 105-e may include a substantially rectangular or square-shaped inner region 610 and an outer region 605. As with the cell collection devices 105 described with reference to FIGS. 3-4, the material properties of the distinct regions 605, 610 of cell collection device 105-e may differ from each other and may be tailored for a particular use.

Figure 7:
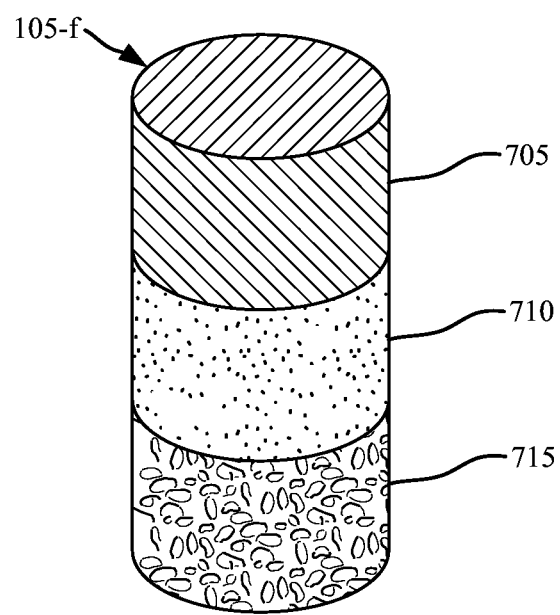
FIG. 7 is an illustration of a cell collection apparatus with multiple distinct regions in accordance with various embodiments.

In various embodiments, the distinct regions of a cell collection device 105 may be stacked or otherwise layered adjacent to each other for certain applications. For example, FIG. 7 shows a substantially cylindrically-shaped cell collection device 105-f with multiple stacked distinct regions in accordance with various embodiments. Cell collection device 105-f may be an example of any cell collection device 105 described in connection with any of FIGS. 1-6. Cell collection device 105-f may include multiple cylindrically-shaped distinct regions 705, 710, 715 that are stacked end to end. Regions 705, 710, 715 may all be made from separate materials and may be joined together by any suitable mechanical or chemical process. Alternatively, regions 705, 710, 715 may be made from the same material where at least one of the material properties of at least one of the regions has been altered by a mechanical or chemical process. Although three distinct regions 705, 710, and 715 are shown, it may be appreciated that any number of cylindrically-shaped regions may be used.

According to various embodiments, at least one of regions 705, 710, and 715 may have at least one material property that differs from at least one material property of at least one other region. For example, region 705 may be more compressible than region 710, which may be more compressible than region 715. Accordingly, if cell collection device 105-f is being withdrawn from an esophagus 210 and passes through a narrow portion requiring circumferential compression of cell collection device 105-f, then each of the regions 705, 710, 715 would compress and exert a pressure against the inside surface of the esophagus proportional to their compressibility. For example, if region 705 is more compressible than region 715, then region 715 may exert a greater pressure on the inside surface of the esophagus than region 705. It may be appreciated that the amount of pressure a region exerts against the inside surface of the esophagus may affect the cell collection characteristics of that region. According to the present example, region 715 may collect more cells, or cells from a deeper layer, or cells that are more difficult to remove from the surface of the body lumen than region 705 due to the increased pressure exerted by region 715. Accordingly, distinct regions 705, 710, 715 may be configured to collect different types of cells or cells from different layers of tissue by manipulating the compression, expansion, and/or roughness characteristics of the various regions.

Figure 8:
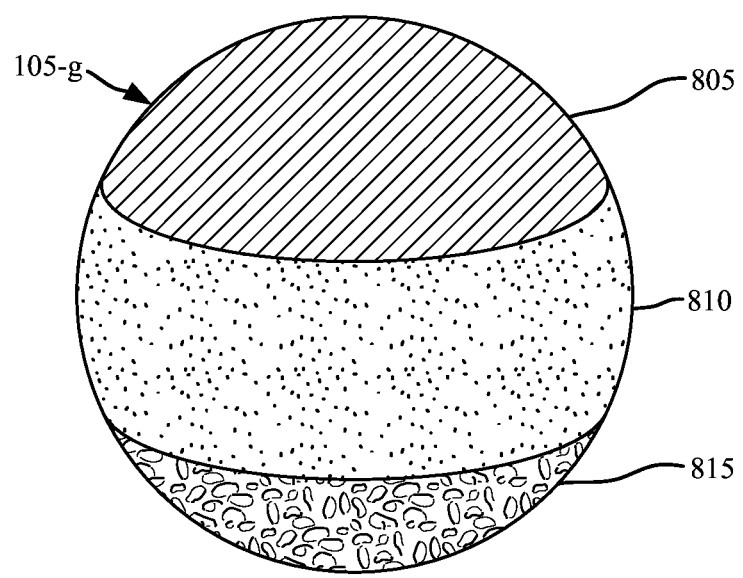
FIG. 8 is an illustration of a cell collection apparatus with multiple distinct regions in accordance with various embodiments.

FIG. 8 shows a spherically-shaped cell collection device 105-g with multiple distinct regions in accordance with various embodiments. Cell collection device 105-g may be an example of any cell collection device 105 described in connection with FIGS. 1-7. Similar to cell collection device 105-f of FIG. 7, cell collection device 105-g may include multiple stacked regions 805, 810, 815. As with the cell collection devices 105 described with reference to FIGS. 3-7, distinct regions 805, 810, 815 may include one or more material properties such that at least one material property of at least one distinct region differs from at least one material property of another distinct region. For example, the roughness or the compressibility of the distinct regions 805, 810, 815 may be configured to collect different types of cells or cells from different layers than each other.

Figure 9:
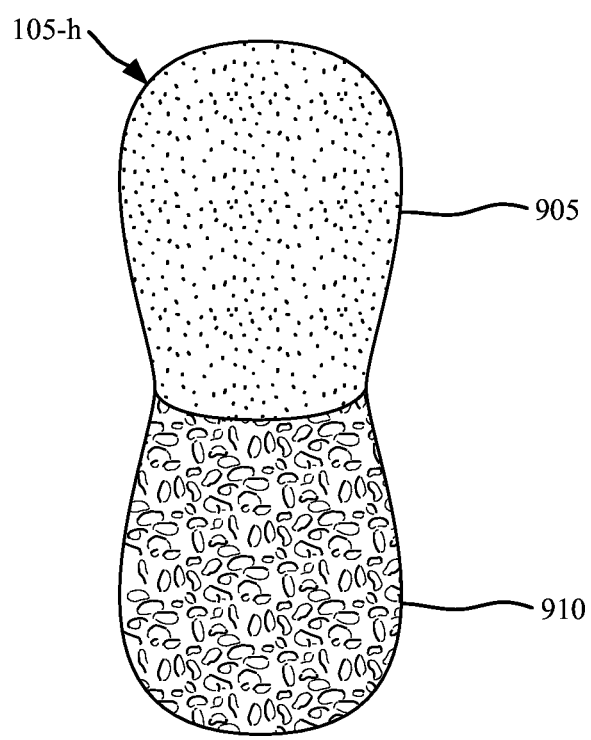
FIG. 9 is an illustration of a cell collection apparatus with multiple distinct regions in accordance with various embodiments.

FIG. 9 shows a peanut-shaped cell collection device 105-$h$ comprising distinct regions 905 and 910 in accordance with various embodiments. As with other described embodiments, regions 905, 910 may have at least one differing material property. The peanut-shaped geometry, in addition to the different material properties of regions 905, 910 of cell collection device 105-$h$, may enhance the cell collection characteristics of the device 105-$h$. Similar to the cell collection device 105-$f$ described with reference to FIG. 7, the various distinct regions 905, 910 of cell collection device 105-$h$ may be configured to exert different pressures on the inside surface of a body lumen, such as an esophagus. For example, region 905 may be more compressible than region 910, which may result in region 910 exerting more pressure on the inside surface of a body lumen than region 905. Additionally, due to the tapered geometry of each region 905, 910, the pressure exerted on the inside surface of the body lumen varies according to which portion of the region is contacting the surface at any given point in time. It may be appreciated that the portion of region 905 with the maximum diameter will exert a greater pressure on the surface of a body lumen than a portion near the middle of cell collection device 105-$h$ that has a smaller diameter. In yet other embodiments, other material properties besides compressibility may differ between distinct regions 905, 910, such as roughness or porosity.

Regarding any of the cell collection devices 105 described in relation to FIGS. 3-9, one or more of the distinct regions may be coated for various purposes. In some embodiments, the leading end of a cell collection device 105 is coated with a lubricant to make the withdrawal of the cell collection device 105 easier and more comfortable for the patient. Referring to cell collection device 105-$f$ of FIG. 7, any of regions 705, 710, 715 may include a lubricant coating. Similarly, with reference to FIG. 9, either of distinct regions 905, 910 may be coated with a lubricant. It may be appreciated that any of the distinct regions described in connection with FIGS. 3-9 may be coated with a lubricant. In accordance with these examples, the other regions not coated with a lubricant may be configured for collecting cells or expanding and compressing the cell collection device 105. Moreover, other coatings may be used in addition to or instead of lubricants. For example, one or more distinct regions of a cell collection device 105 may be coated with an analgesic or other pain relieving medicine to reduce the pain caused to the patient by removing cells from a body lumen. In other examples one or more distinct regions may be coated with an antibiotic or hydrophilic substance. It may be appreciated that any type or number of liquid or gel substances may be coated or otherwise applied to one or more distinct regions of a cell collection device 105 for purposes of applying or otherwise delivering the substance to the inside of a targeted body lumen.

As mentioned with reference to FIGS. 1-2, according to various embodiments, the geometry of a cell collection device 105 may be configured to enhance the cell collection properties or the compression and expansion properties of the device. For example, a cell collection device 105 may include one or more tapered features such that one end of the cell collection device 105 has a larger diametric dimension than the opposite end. Furthermore, in some embodiments, a cell collection device 105 may include one or more cavities or similar features that reduce the compressible volume of the cell collection device 105, such that the device 105 may be compressed and encased within a smaller capsule 115. Reducing the size of the capsule 115 may increase the swallowability of the capsule 115, thereby reducing discomfort to the patient.

Figure 10A:
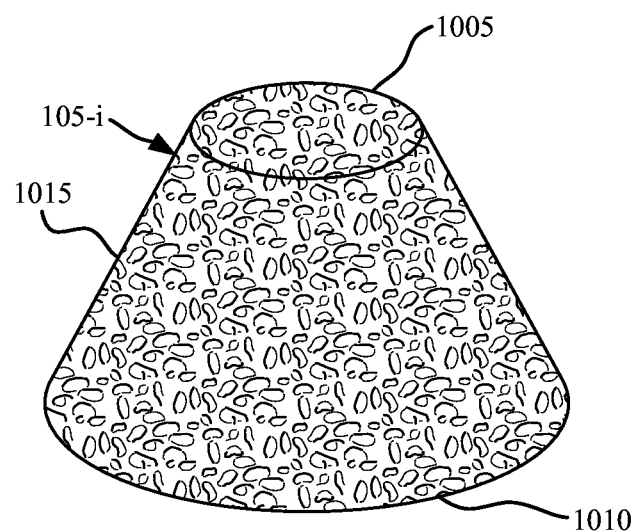
FIG. 10A is an illustration of a cell collection apparatus with a tapered geometry in accordance with various embodiments.
Figure 10B:
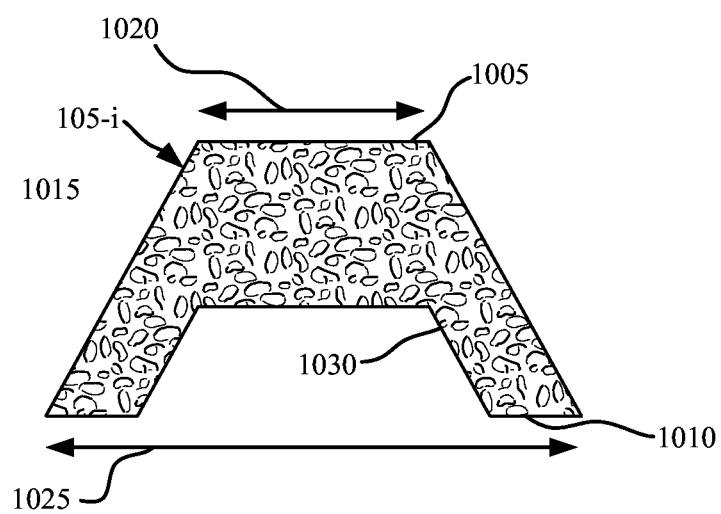
FIG. 10B is an illustration of a cell collection apparatus with a tapered geometry and a cavity in accordance with various embodiments.

With reference to FIG. 10A, a cell collection device 105-$i$ is shown in accordance with various embodiments. Cell collection device 105-$i$ may be an example of a cell collection device 105 described in connection with any of FIGS. 1-9. Accordingly, cell collection device 105-$i$ may be made from an abrasive material configured to collect cells from a body lumen by scraping a surface of the body lumen. As shown in FIG. 10A, cell collection device 105-$i$ may include a bottom end 1010 that is substantially flat with a diameter 1025 and a top end 1005 that is substantially flat with a diameter 1020 (as shown in FIG. 10B). In various embodiments, diameter 1020 of top end 1005 is smaller than the diameter 1025 of bottom end 1010 such that the outer surface 1015 of cell collection device 105-$i$ is tapered from top end 1005 to bottom end 1010 thereby forming a conical frustum. In accordance with the present example, as cell collection device 105-$i$ is being withdrawn from the body lumen (with top end 1005 as the leading end), the outer surface 1015 may collect cells from the body lumen by scraping the surface of the body lumen.

Referring to the cross sectional view of FIG. 10B, cell collection device 105-$i$ includes a cavity 1030 in some embodiments. Cavity 1030 may extend from the bottom end 1010 of the device 105-$i$ towards the top end 1005. The geometric shape of the cavity 1030 may match that of the cell collection device 105-$i$ in some embodiments. Accordingly, cavity 1030 may be substantially shaped as a conical frustum. However, it may be appreciated that cavity 1030 may be any shape, such as a cylinder, a sphere, a paraboloid, a cone, or any combination of these shapes. It may be apparent that the inclusion of a cavity 1030 will reduce the amount of material that makes up cell collection device 105-$i$. Accordingly, cell collection device 105-$i$ may be compressed within a smaller capsule 115 than if the device 105-$i$ was solid throughout, thereby increasing the swallowability of the device 105-$i$.

Figure 11A:
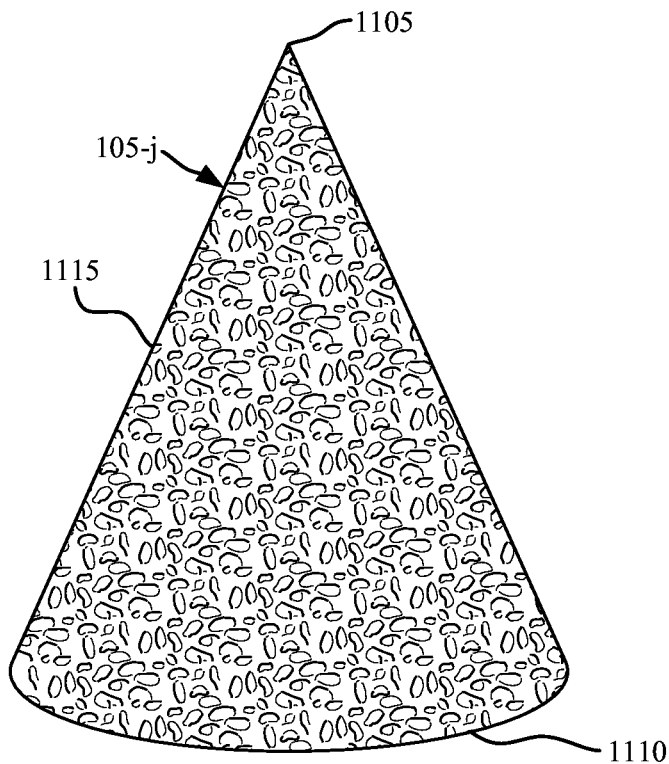
FIG. 11A is an illustration of a cell collection apparatus with a tapered geometry in accordance with various embodiments.
Figure 11B:
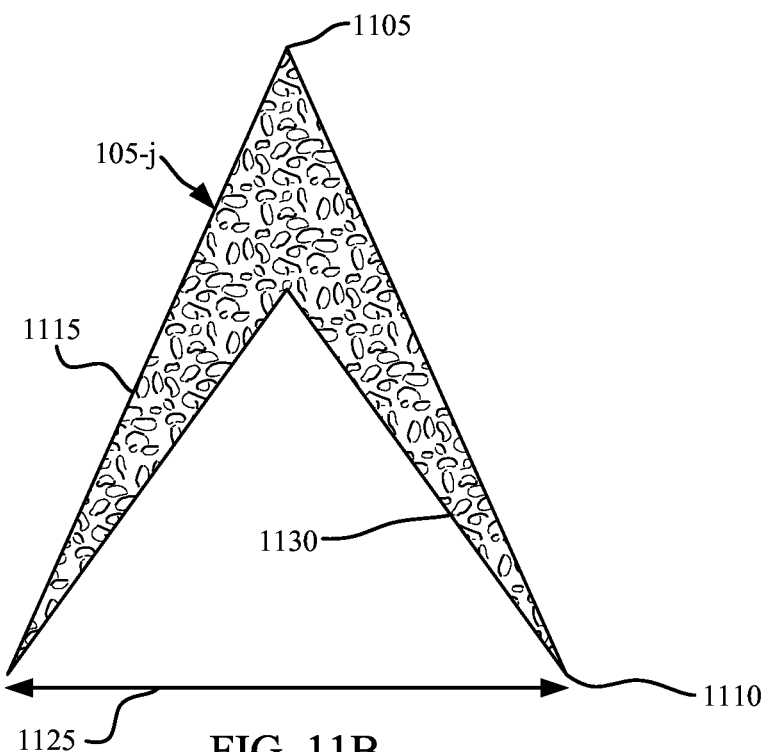
FIG. 11B is an illustration of a cell collection apparatus with a tapered geometry and a cavity in accordance with various embodiments.

Turning to FIG. 11A, a conical-shaped cell collection device 105-$j$ is shown in accordance with various embodiments. Cell collection device 105-$j$ may be an example of any cell collection device 105 discussed in connection with any of FIGS. 1-10. Cell collection device 105-$j$ may include a bottom end 1110 with a diameter 1125 (as shown in FIG. 11B) and a pointed top end 1105 such that the outer surface 1115 tapers from the top end 1105 to the bottom end 1110 thereby forming a substantially conical-shaped device. As shown in the cross sectional view of FIG. 11B, according to various embodiments, cell collection device 105-$j$ may also include a cavity 1130 extending from bottom end 1110 towards the top end 1105. In some embodiments, cavity 1130 is conically shaped. However, a variety of shapes may be used including a conical frustum, a cylinder, a sphere, a paraboloid, or any combination of these shapes.

Figure 12A:
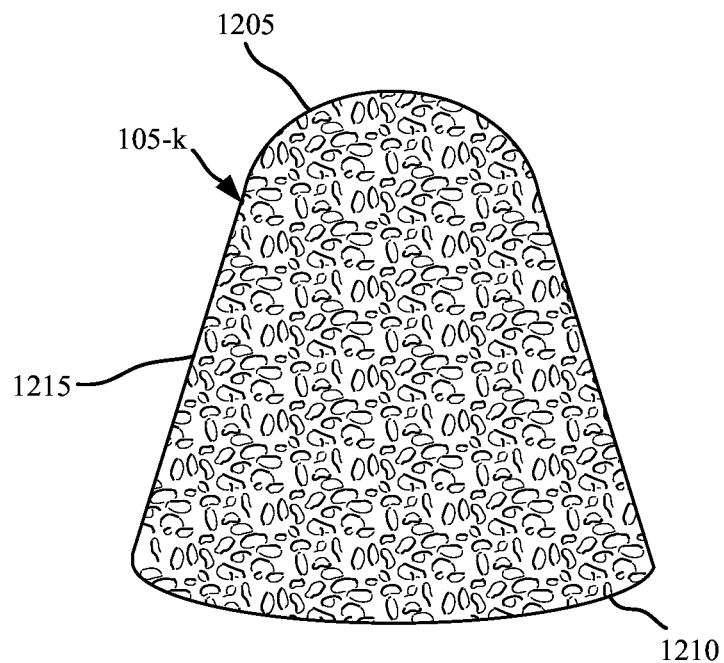
FIG. 12A is an illustration of a cell collection apparatus with a tapered geometry in accordance with various embodiments.
Figure 12B:
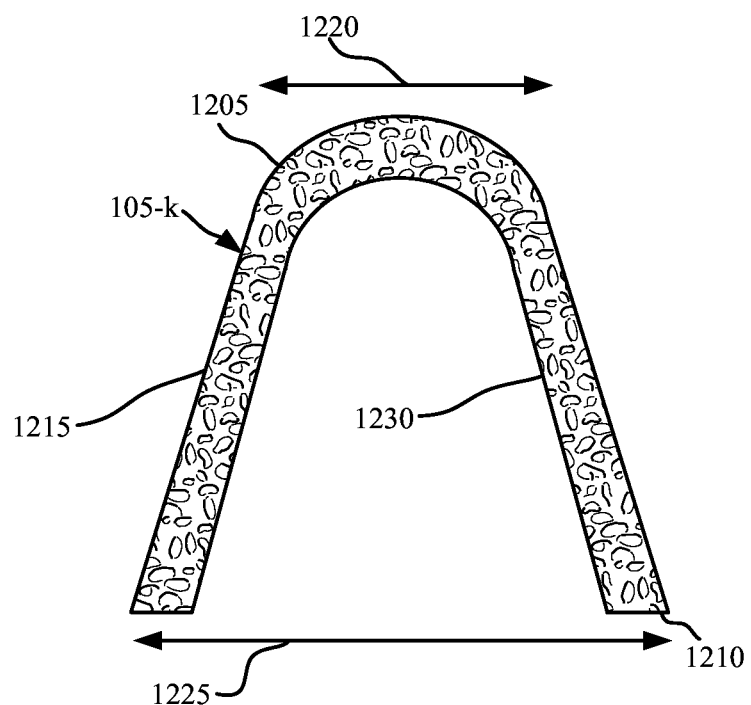
FIG. 12B is an illustration of a cell collection apparatus with a tapered geometry and a cavity in accordance with various embodiments.

With reference to FIG. 12A, a substantially paraboloid-shaped cell collection device 105-$k$ is shown in accordance with various embodiments. Cell collection device 105-$k$ may be an example of any cell collection device described in connection with FIGS. 1-11. Cell collection device 105-$k$ may include a bottom end 1210 with a diameter 1225 that is larger than a diameter 1220 of top end 1205 (as shown in FIG. 12B). Accordingly, outer surface 1215 is tapered from the top end 1205 to the bottom end 1210. As shown in the cross sectional view of FIG. 12B, according to various embodiments, cell collection device 105-k may also include a cavity 1230 extending from the bottom end 1210 toward top end 1205. Cavity 1230 may be shaped substantially as a paraboloid, cone, cylinder, sphere, or any combination of these shapes.

Figure 13A:
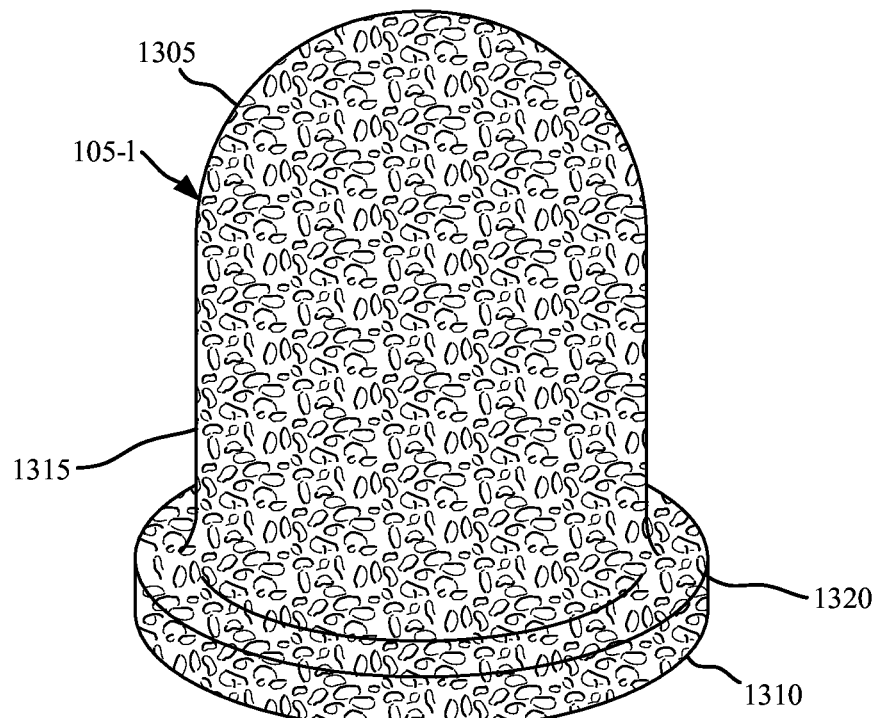
FIG. 13A is an illustration of a cell collection apparatus with a tapered geometry in accordance with various embodiments.
Figure 13B:
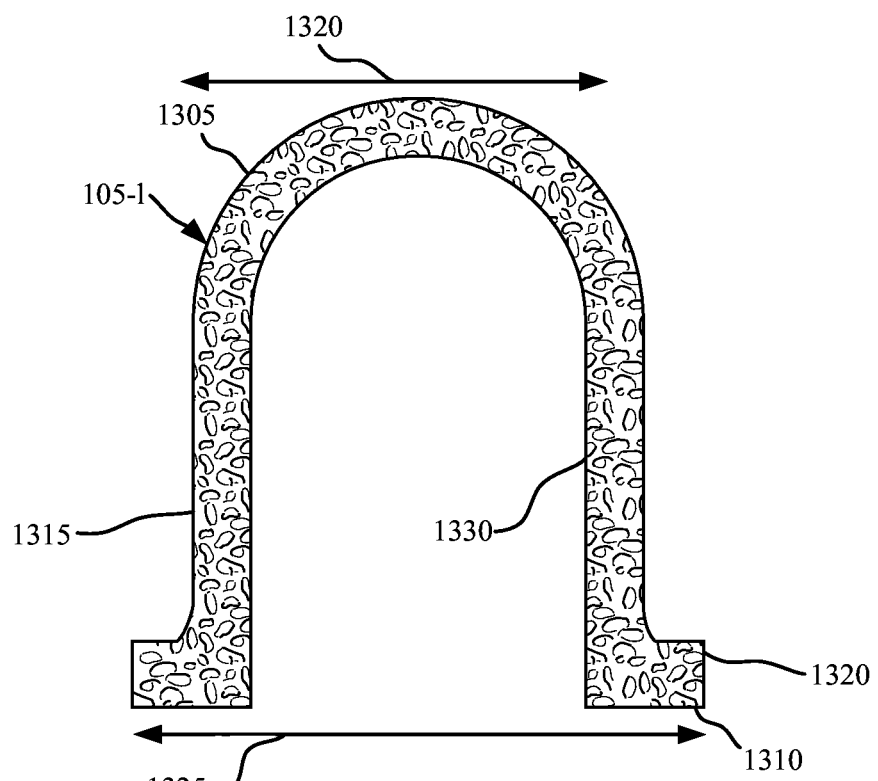
FIG. 13B is an illustration of a cell collection apparatus with a tapered geometry and a cavity in accordance with various embodiments.

With reference to FIG. 13A, a cell collection device 105-l is shown in accordance with various embodiments. Cell collection device 105-l may be an example of any cell collection device 105 described with reference to FIGS. 1-12. As shown in FIG. 13A, cell collection device 105-l may be substantially bell-shaped with a rim or flange 1320 arranged circumferentially around outer surface 1315 and flush with the bottom end 1310. In some embodiments, flange 1320 may only extend around a partial circumference of the outer surface 1315 or may include equally spaced gaps around the circumference. As illustrated in the cross sectional view of FIG. 13B, in accordance with various embodiments, cell collection device 105-l may include a cavity 1330 extending from the bottom end 1310 towards the top end 1305. Cavity 1330 may be shaped substantially as a bell, paraboloid, sphere, cone, conical frustum, or any combination of these shapes. Moreover, in various embodiments, flange 1320 may be combined with any cell collection device 105 described in relation to FIGS. 10-12. For example, flange 1320 may be circumferentially arranged around the outer surface 1015 and flush with bottom end 1010 of cell collection device 105-i described in connection with FIG. 10.

Figure 14A:
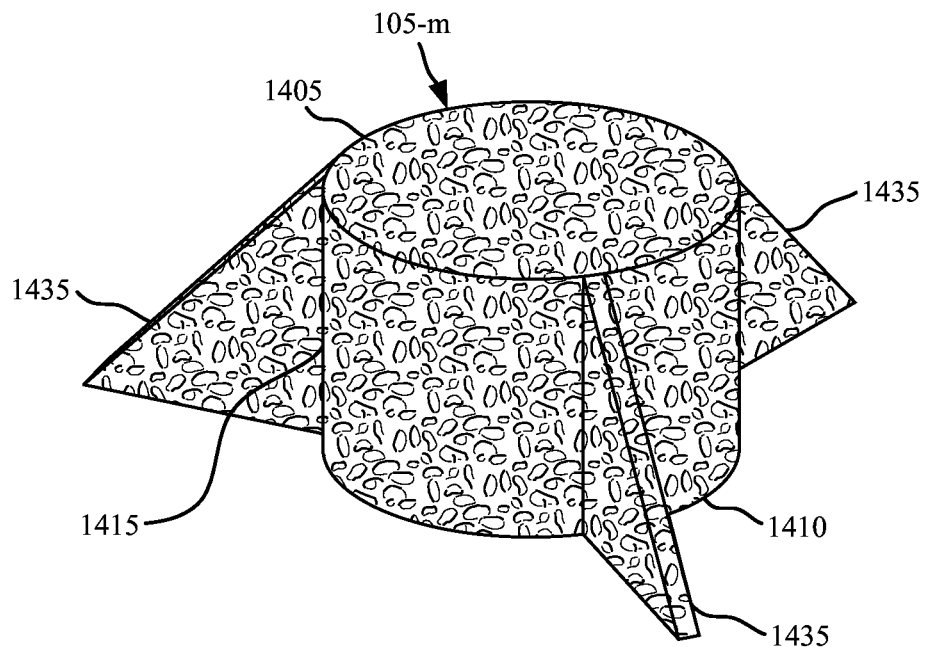
FIG. 14A is an illustration of a cell collection apparatus with a tapered geometry in accordance with various embodiments.
Figure 14B:
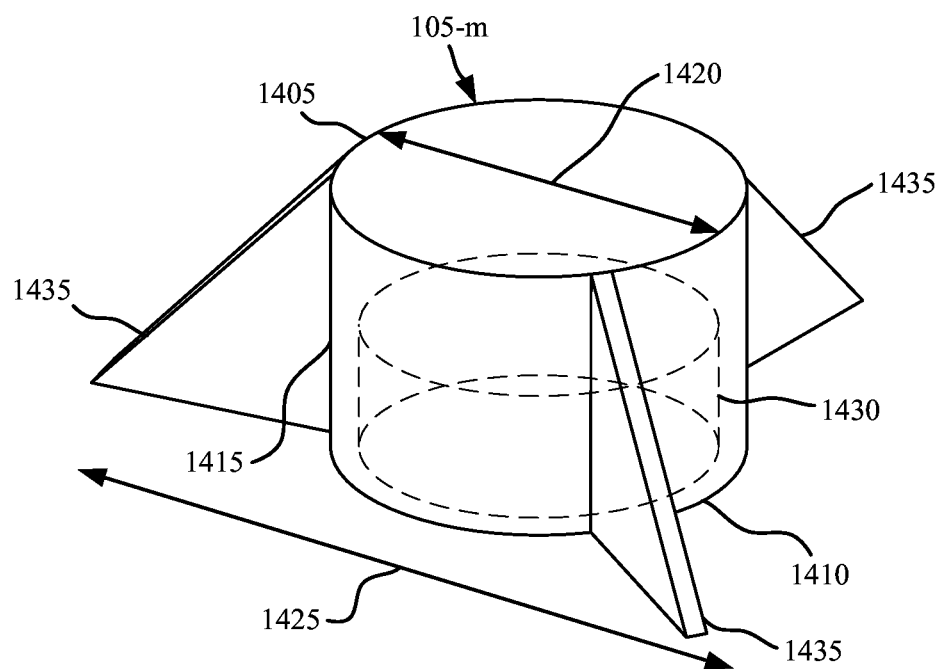
FIG. 14B is an illustration of a cell collection apparatus with a tapered geometry and a cavity in accordance with various embodiments.

With reference to FIG. 14A, a cell collection device 105-m is shown with one or more tapered features in accordance with various embodiments. Cell collection device 105-m may be an example of any cell collection device 105 described in connection with FIGS. 1-13. Cell collection device 105-m may be generally cylindrically-shaped with a substantially flat top end 1405 with a diameter 1420 (as shown in FIG. 14B). The cylindrical portion of cell collection device 105-m may also include a substantially flat bottom end 1410 with the same diameter 1420 as the top end 1405. Additionally, cell collection device 105-m may include one or more tapered portions or fins 1435. Fins 1435 may be adhered to or otherwise coupled with the exterior cylindrical surface 1415 of the cell collection device 105-m. Alternatively, fins 1435 may be formed out of the same material as the rest of cell collection device 105-m during the manufacturing process.

In some embodiments, three fins 1435 are spaced at even radial increments (every 120 degrees) around the outside surface 1415 of cell collection device 105-m. In such embodiments, as cell collection device 105-m is being retrieved from a body lumen (with top end 1405 end as the leading end) the fins 1435 may keep the cell collection device 105-m relatively centered with respect to the body lumen. If the fins 1435 are evenly spaced around the circumference of cell collection device 105-m, the fins 1435 may form a diameter 1425 (as shown in FIG. 14B) at the bottom end 1410 that is larger than the diameter 1420 of the top end 1405. As such, fins 1435 taper from diameter 1420 at top end 1405 to a larger diameter 1425 at bottom end 1410. In other embodiments, fins 1435 may be asymmetrically arranged about the outer cylindrical surface 1415 such that cell collection device 105-m is biased towards one side of the body lumen while being retrieved from the body lumen. However, it may be appreciated that any number of fins 1435 may be used with any spacing configuration.

As shown in FIG. 14B, in some embodiments, cell collection device 105-m may include a cavity 1430 extending from bottom end 1410 towards top end 1405. Cavity 1430 may be shaped substantially as a cylinder, cone, conical frustum, paraboloid, or any combination of these shapes. Moreover, it may be appreciated that fins 1435 may be combined with any of the tapered cell collection devices 105 described in connection with FIGS. 10-13. For example, fins 1435 may be circumferentially arranged around outer surface 1015 of cell collection device 105-i described in connection with FIG. 10 or around outer surface 1315 of cell collection device 105-l described with reference to FIG. 13.

As described with reference to FIG. 1A, a retrieval string 110 may be coupled with a cell collection device 105, such as any cell collection device 105 described in connection with FIGS. 10-14. The retrieval string 110 may be tied, adhered, or otherwise coupled with a cell collection device 105. For example, with reference to FIG. 10A, a string 110 may be threaded down through top end 1005 for a portion of the way through the material and then back up through the top end 1005 thereby hooking or grasping a portion of the cell collection device material. The free end of string 110 may be tied or otherwise fastened to itself or cell collection device 105-i to adequately secure the string 110 to the cell collection device 105-i so that the string 110 may safely retrieve cell collection device 105-i from a body lumen. It may be appreciated that threading a retrieval string 110 through a cell collection device 105 as just described may be easier for embodiments with a cavity. For example, referring to FIG. 10B, a retrieval string 110 may be threaded through the top end 1005 into the cavity 1030 and then back up through and out of the top end 1005. In other examples, retrieval string 110 may be threaded from the top end 1005 and into cavity 1030, where a plug or washer-like element is attached to the free end of the retrieval string 110 such that the string 110 is not able to be pulled back through the top end 1005.

It may be appreciated that any of the tapered cell collection devices 105 described in connection with FIGS. 10-14 may include multiple distinct regions with different material properties as described in connection with FIGS. 3-9. For example, any of cell collection devices 105-i-105-m may include a wedge-shaped region as described in connection with FIG. 3. In some embodiments, any of cell collection devices 105-i-105-m may include one or more inner regions as described in connection with FIG. 4-6. For example, instead of having a cavity or other hollowed portion, any of cell collection devices 105-i-105-m may include an inner region with a different compressibility than the outer region. In yet other embodiments, any of cell collection devices 105-i-105-m may include one or more stacked regions as described in connection with FIGS. 7-9. As another example, with reference to cell collection device 105-m of FIG. 14, fins 1435 may have a different roughness, compressibility, or porosity than the rest of cell collection device 105-m. In other embodiments, some fins 1435 may have different roughness or compression properties than other fins 1435 so that each fin 1435 may be configured to collect a different type of cell or tissue layer from the body lumen as described in connection with FIG. 7.

As mentioned with reference to FIGS. 1-2, the natural expansion properties of a conventional cell collection device may be inadequate in certain instances. For example the sponge material of a typical collection device may suffer from mechanical creep after being compressed within a capsule for an extended period of time, which may reduce the ability of the sponge material to expand to its original, pre-compressed size once released from the capsule. This may result in a sponge that is too small to adequately collect cells from a body lumen, such as the gastrointestinal tract. Additionally, a typical sponge may lack the ability to adequately push on the inside of the capsule wall to help break open the capsule. This may result in an extended capsule dissolution time, which will increase the time of the procedure and thus the discomfort of the patient. Also, the natural expansion properties of the cell collection material may be inadequate to exert a sufficient force on the internal wall of a body lumen to collect cells. Accordingly, some embodiments of a cell collection device 105 may include one or more expansion elements configured to expand the cell collection device from a compressed configuration.

Figure 15A:
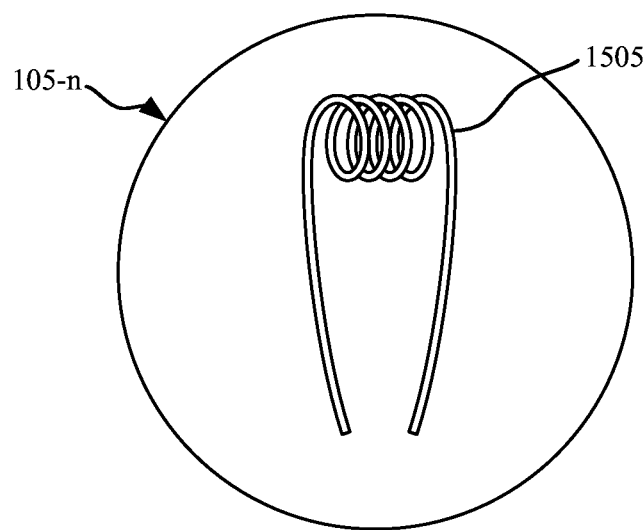
FIG. 15A is an illustration of a cell collection apparatus with one or more expansion elements in a compressed configuration in accordance with various embodiments.

With reference to FIG. 15A, a cell collection device 105-*n* including an expansion element 1505 is shown in a compressed configuration in accordance with various embodiments. Cell collection device 105-*n* may be an example of any cell collection device 105 described in connection with FIGS. 1-14. Accordingly, in some embodiments, cell collection device 105-*n* is made from an abrasive and substantially non-absorbent material configured to collect cells from a body lumen by scraping a surface of the body lumen. A compressed configuration may refer to the configuration when the cell collection device 105 is compressed within a capsule 115. However, a compressed configuration may refer to any configuration where at least one dimension of the cell collection device 105 is smaller than when the cell collection device 105 is in its natural or expanded configuration. Referring to FIG. 15A, according to various embodiments, cell collection device 105-*n* may include an expansion element 1505 disposed within the cell collection device 105-*n*. Expansion element 1505 may be placed within the cell collection device 105-*n* after the cell collection device 105-*n* has been manufactured, or, in some embodiments, the cell collection device 105-*n* may be manufactured with expansion element 1505 already in place. Furthermore, the expansion element 1505 may be implanted into the material of the cell collection device 105-*n*, or the expansion element 1505 may be placed within a hollowed portion or cavity inside the cell collection device 105-*n*.

Figure 15B:
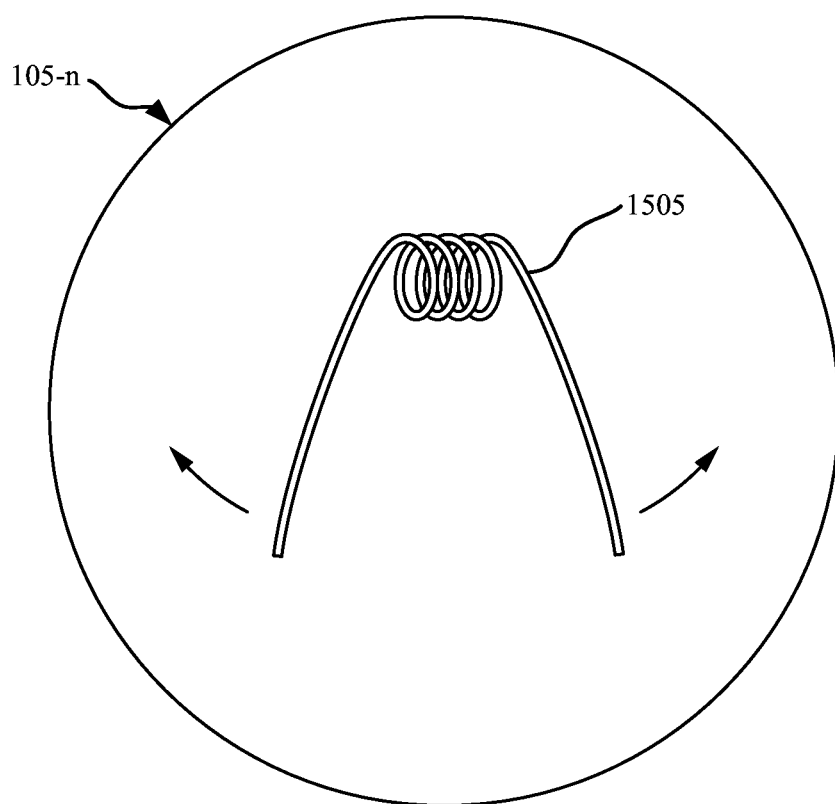
FIG. 15B is an illustration of a cell collection apparatus with one or more expansion elements in an expanded configuration in accordance with various embodiments.

Expansion element 1505 may be any apparatus, device, or material that expands or assists in the expansion of a cell collection device 105 from a compressed configuration to an expanded configuration. In various embodiments, expansion element 1505 stores a form of elastic potential energy that is converted into mechanical work to expand the cell collection device 105-*n* from a compressed configuration into an expanded configuration. For example, as illustrated in FIG. 15B, expansion element 1505 may expand outward to help expand cell collection device 105-*n* into an expanded configuration. In some embodiments, expansion element 1505 is a spring, stent, or any other element capable of storing elastic potential energy. For example, as shown in FIGS. 15A-15B, expansion element 1505 may be a torsion spring. Moreover, in some embodiments, expansion element 1505 may include a material that changes shape based upon a change in temperature. For example, nitinol may be used to form an expansion element 1505 that expands by returning to an initial shape after being heated to an activation temperature. In other embodiments, the expansion element 1505 is made from a superelastic material that naturally expands the cell collection device 105-*n* when unconstrained by a capsule 115. According to certain aspects, nitinol is used as the superelastic material.

Figure 16:
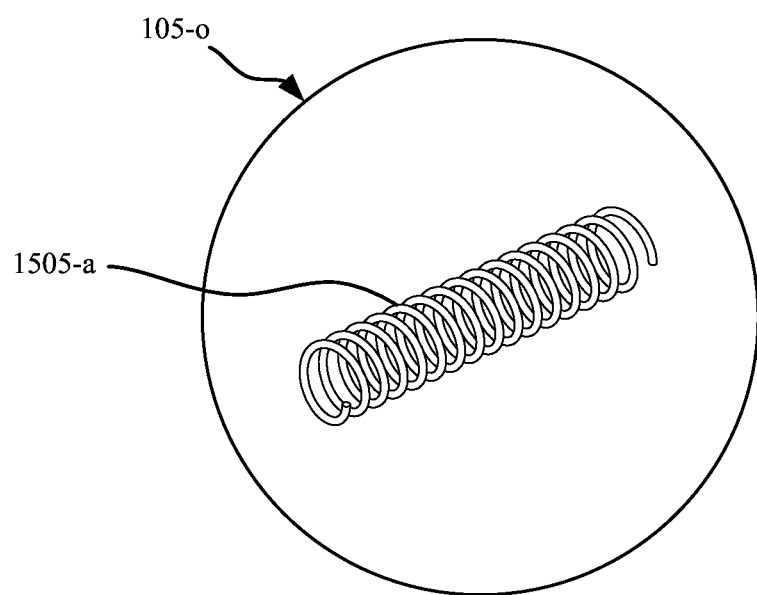
FIG. 16 is an illustration of a cell collection apparatus with one or more expansion elements in accordance with various embodiments.

In another example, as illustrated by FIG. 16, cell collection device 105-*o* may include an expansion element 1505-*a* in the form of a helical spring. Cell collection device 105-*o* may be an example of any cell collection device described with reference to FIGS. 1-15 and expansion element 1505-*a* may be an example of expansion element 1505 described in connection with FIG. 15. It may be appreciated that any other type of spring may be used, such as a leaf spring.

Figure 17:
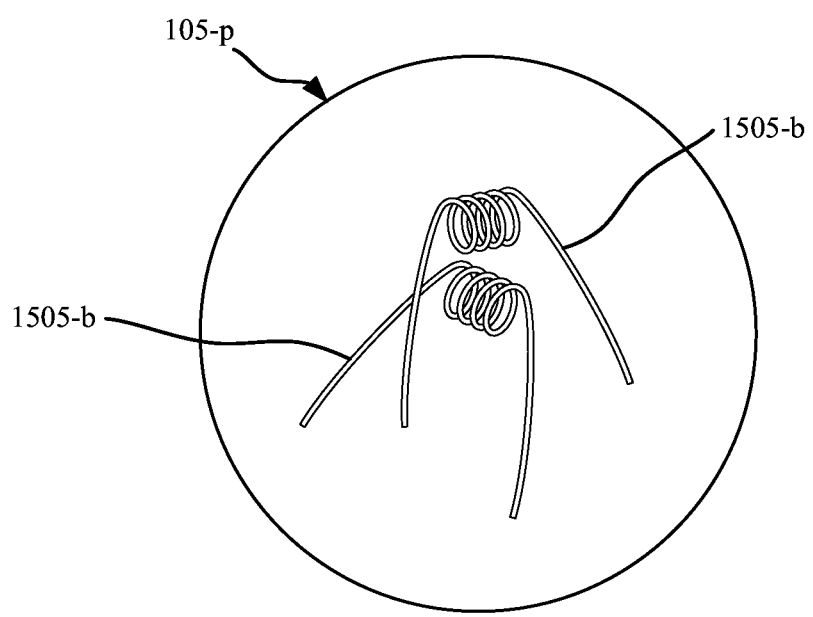
FIG. 17 is an illustration of a cell collection apparatus with one or more expansion elements in accordance with various embodiments.

In accordance with various embodiments, a cell collection device 105 may include multiple expansion elements 1505 either arranged within or on an outside surface of cell collection device 105. For example, with reference to FIG. 17, a cell collection device 105-*p* with two expansion elements 1505-*b* is shown, according to various embodiments. Cell collection device 105-*p* may be an example of any cell collection device 105 described in connection with any of FIGS. 1-16 and expansion elements 1505-*b* may be examples of any expansion element 1505 described in connection with FIGS. 15-16. As shown in FIG. 17, expansion elements 1505-*b* may be torsion springs, but expansion elements 1505-*b* may also comprise leaf or helical springs. According to various embodiments, the expansion elements 1505-*b* are arranged and configured to expand cell collection device 105-*p* circumferentially. For example, expansion elements 1505-*b* may be arranged orthogonal to each other such that expansion elements 1505-*b* provide outward force in four opposing directions. It may be appreciated that instead of torsion springs, two helical springs may be arranged orthogonal to each other to provide outward expansion force in four opposing directions.

Figure 18:
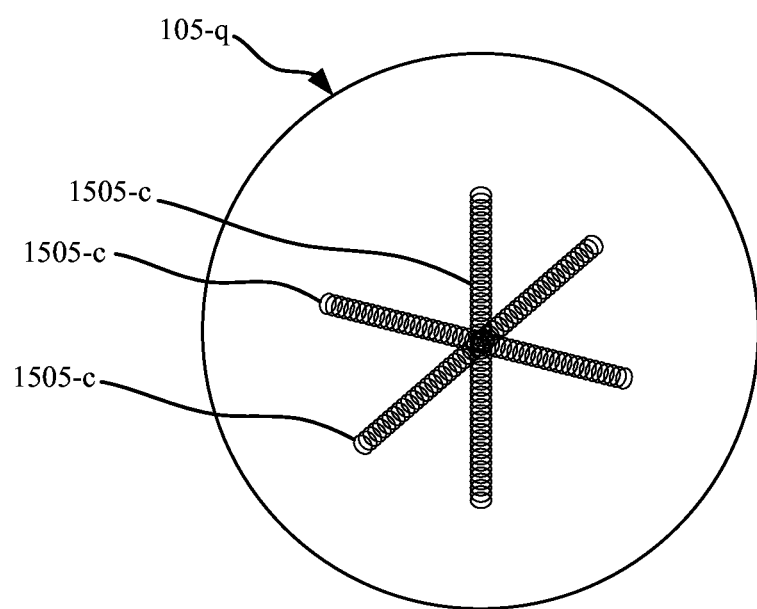
FIG. 18 is an illustration of a cell collection apparatus with one or more expansion elements in accordance with various embodiments.

With reference to FIG. 18, a cell collection device 105-*q* with three expansion elements 1505-*c* is shown in accordance with various embodiments. Cell collection device 105-*q* may be an example of any cell collection device 105 described with reference to any of FIGS. 1-17. Expansion elements 1505-*c* may be helical springs, or they may be any other type of spring or expansion element 1505 described in connection with FIGS. 15-17. Furthermore, expansion elements 1505-*c* may be arranged orthogonal to each other such that they provide expansion force in six opposing directions. Accordingly, expansion elements 1505-*c* may be arranged and configured to spherically expand cell collection device 105-*q*.

Figure 19A:
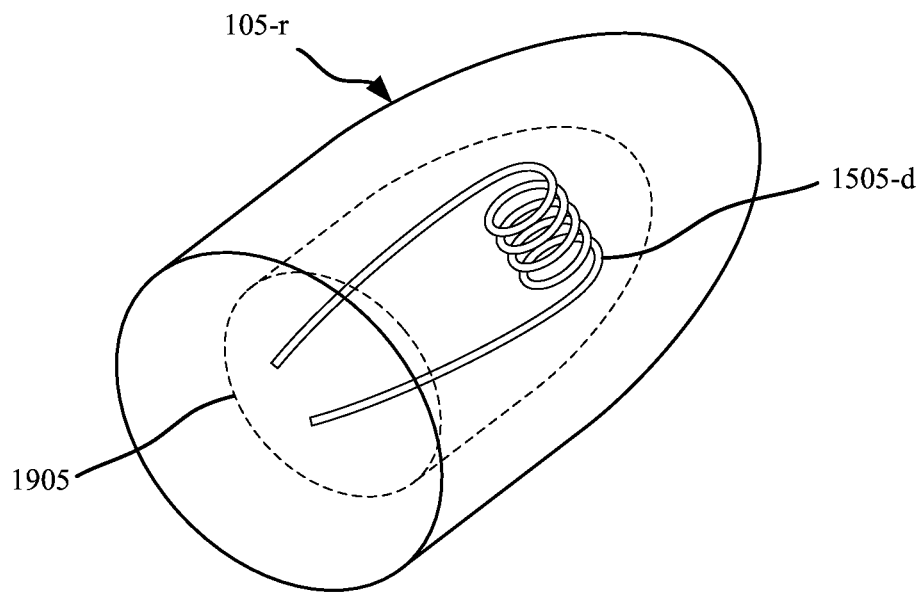
FIG. 19A is an illustration of a cell collection apparatus with one or more expansion elements in accordance with various embodiments.
Figure 19B:
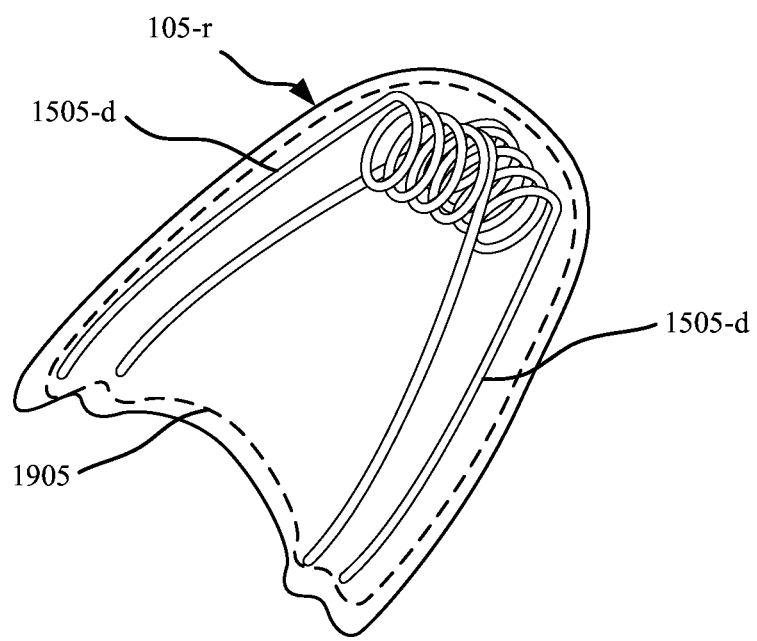
FIG. 19B is an illustration of a cell collection apparatus with one or more expansion elements in accordance with various embodiments.

With reference to FIG. 19A, a cell collection device 105-*r* is shown with a cavity 1905 or other hollowed portion configured to house an expansion element 1505-*d*, in accordance with various embodiments. The cavity 1905 may extend to a portion of the outside surface of the cell collection device 105-*r* or, in other examples, the cavity 1905 may be sealed off from the outside surface of the cell collection device 105-*r* such that the cavity 1905 is completely encapsulated by the material of the cell collection device 105-*r*. Cell collection device 105-*r* may be an example of any cell collection device 105 described in connection with any of FIGS. 1-18 and expansion element 1505-*d* may be an example of any expansion element 1505 described in connection with any of FIGS. 15-18. As shown in FIG. 19A, expansion element 1505-*d* may be a torsion spring. However, it may be appreciated that expansion element 1505-*d* may comprise any expansion element 1505 described in connection with any of FIGS. 15-16. Moreover, multiple expansion elements 1505 may be housed within cavity 1905 in various configurations and orientations as described in connection with FIGS. 17-18 (as shown in FIG. 19B).

The size of cavity 1905 with respect to the overall size of cell collection device 105-*r* may be varied according to various embodiments. It may be appreciated that by varying the size of the cavity 1905, the thickness of the wall between cavity 1905 and the outer surface of cell collection device 105-*r* may be varied. For example, as shown in FIG. 19A, the wall of material between cavity 1905 and the outer surface of cell collection device 105-*r* may be relatively thick. In contrast, as shown in FIG. 19B, the wall thickness of material between cavity 1905 and the outer surface of cell collection device 105-*r* may be relatively thin.

Figure 19C:
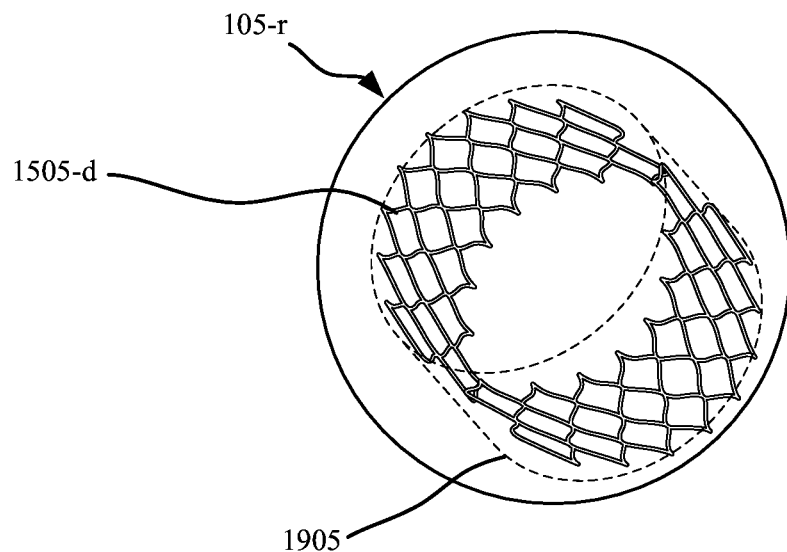
FIG. 19C is an illustration of a cell collection apparatus with one or more expansion elements in accordance with various embodiments.

Turning to FIG. 19C, another embodiment of cell collection device 105-*r* is illustrated. In accordance with various embodiments, the expansion element 1505-*e* is a stent, frame, cage, basket, or other similar element sized to fit within the cavity 1905 and configured to expand the cell collection device 105-*r* from a compressed configuration to an expanded configuration. In some embodiments, the stent expansion element 1505-*e* is cylindrical in shape, as shown in FIG. 19C, to correspond with the cylindrical-shaped cavity 1905.

Figure 19D:
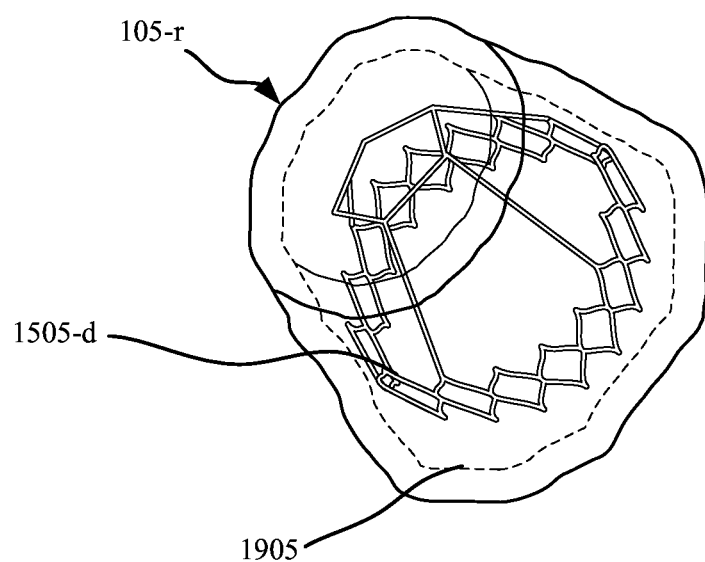
FIG. 19D is an illustration of a cell collection apparatus with one or more expansion elements in accordance with various embodiments.

In yet another embodiment, shown in FIG. 19D, the stent expansion element 1505-*e* may be shaped as a conical frustum or lampshade to correspond to a similarly-shaped cavity 1905 and/or cell collection device 105-*r*. It may be appreciated that, in addition to cylindrical and conical frustum shapes, the stent expansion element 1505-*e* may be formed into a conical, spherical, or bell shape to conform to the shape and size of the cavity 1905.

In some embodiments, the stent expansion element 1505-*e* is made from a super elastic material, such as nitinol for example.

Figure 20:
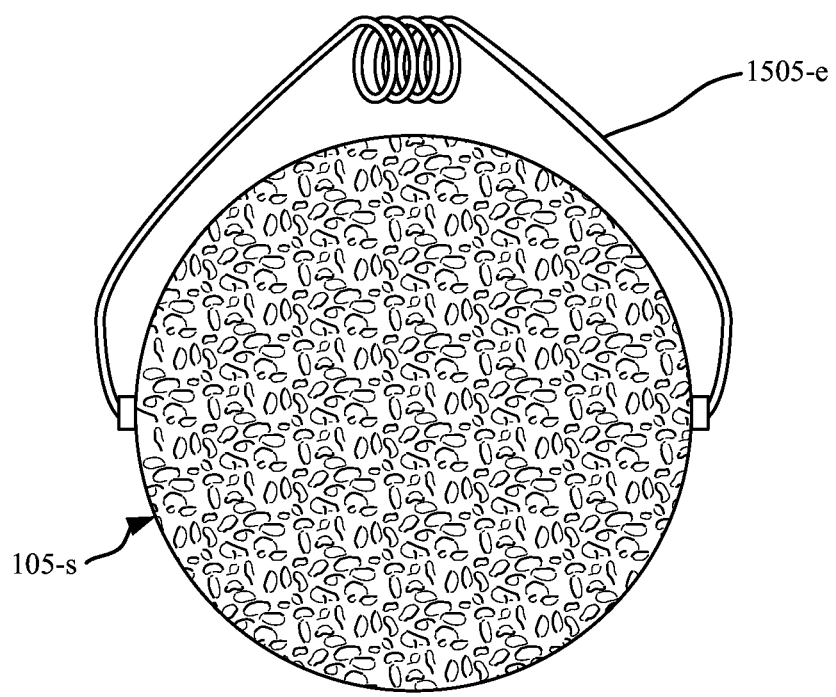
FIG. 20 is an illustration of a cell collection apparatus with one or more expansion elements in accordance with various embodiments.

According to various embodiments, a cell collection device 105 may include one or more expansion elements 1505 coupled to an outside surface of the cell collection device 105. For example, with reference to FIG. 20, a cell collection device 105-*s* with an expansion element 1505-*f* coupled with an outside surface of cell collection device 105-*s* is shown in accordance with various embodiments. Cell collection device 105-*s* may be an example of any cell collection device 105 described in connection with any of FIGS. 1-19. As shown in FIG. 20, expansion element 1505-*f* may comprise a torsion spring, but any of the expansion elements 1505 described in connection with FIGS. 15-16 may also be used. Furthermore, expansion element 1505-*f* may be a rubber band or any elastic member that provides a tension force. Moreover, multiple expansion elements 1505 may be coupled with an outside surface of cell collection device 105-*s* in a variety of orientations and configurations as described in connection with FIGS. 17-18. For example, two or more expansion elements 1505-*f* may be arranged on an outside surface of cell collection device 105-*s* and may be configured to circumferentially expand cell collection device 105-*s* from a compressed configuration.

Figure 21:
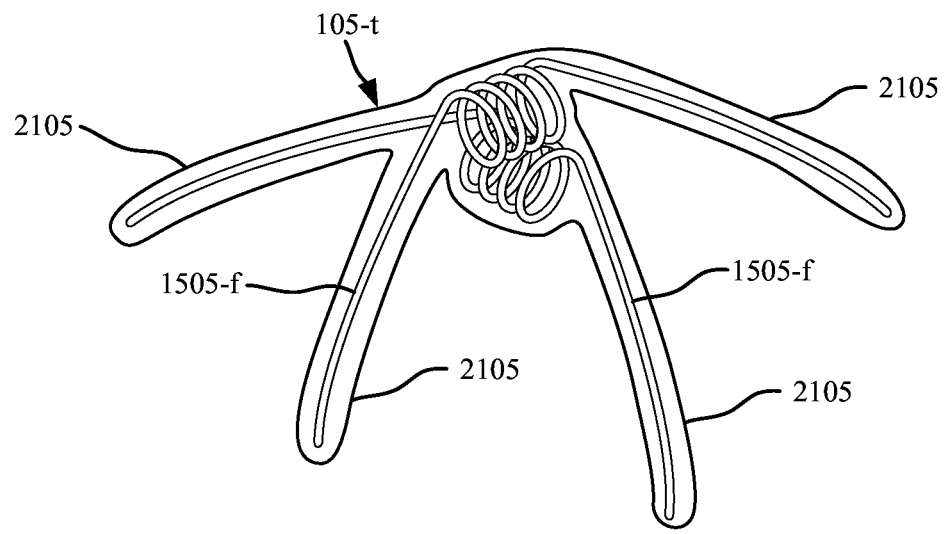
FIG. 21 is an illustration of a cell collection apparatus with one or more expansion elements in accordance with various embodiments.

Turning to FIG. 21, a cell collection device 105-*t* is shown in accordance with various embodiments. Cell collection device 105-*t* may include one or more expansion elements 1505-*g*, which may be examples of any expansion element 1505 described in relation to FIGS. 15-16. As shown in FIG. 21, expansion elements 1505-*g* may comprise two torsion springs arranged orthogonal to each other forming four legs 2105. Each of the four legs 2105 may be surrounded by the abrasive material of cell collection device 105-*t*. Accordingly, as cell collection device 105-*t* is being retrieved from a body lumen, only the relatively small surface area of each of the four legs 2105 will make contact with the inside surface of the body lumen to collect cells or other tissue.

It may be appreciated that the expansion elements 1505 as described in FIGS. 15-21 may be coupled with any of the cell collection devices described in any of FIGS. 1-14. For example, one or more expansion elements 1505 may be disposed within or coupled to an outside surface of any of cell collection devices 105-*b*-105-*h* with multiple distinct regions as described with reference to FIGS. 3-9. For example, as described in connection with FIG. 4, inner region 410 may be highly compressible whereas outer region 405 may be less compressible but relatively abrasive for scraping and removing cells from a surface of a body lumen. It may be appreciated that due to a highly compressible inner region 410, cell collection device 105-*c* may be more easily compressed within a smaller capsule 115. However, the highly compressible nature of inner region 410 may also reduce the ability of cell collection device 105-*c* to expand fully to its pre-compressed size once released from the capsule 115. Accordingly, in some embodiments, an expansion element 1505 such as a torsion spring, helical spring, or stent may be disposed within inner region 410 and configured to expand cell collection device 105-*c* from a compressed configuration.

In other embodiments, one or more expansion elements 1505 may disposed within or coupled to an outside surface of any of cell collection devices 105-*i*-105-*m* as described with reference to FIGS. 10-14. In embodiments where the cell collection device 105 is solid throughout, an expansion element 1505 may be disposed within the device 105 as described in connection with FIGS. 15-16. Moreover, according to several embodiments, multiple expansion elements 1505 may be disposed within any of cell collection devices 105-*i*-105-*m* in various orientations and configurations as described with reference to FIGS. 17-18. In embodiments where any of cell collection devices 105-*i*-105-*m* is configured with an internal cavity or other hollowed portion, it may be appreciated that one or more expansion elements 1505 may be disposed within the cavity as described in connection with FIGS. 19A-19D.

As mentioned with reference to FIGS. 1-2, according to various embodiments, multiple cell collection devices 105 may be placed in a body lumen and retrieved simultaneously to collect cells or tissue from the body lumen. Using multiple cell collection devices 105 simultaneously may increase the accuracy and reliability of a cell collection procedure. For example, the multiple cell collection devices 105 may be configured to adapt to the local size and shape of the body lumen by being grouped and ungrouped within the body lumen. Furthermore, since multiple cell collection devices 105 are being used, each cell collection device 105 may be smaller than a typical cell collection device 105, thereby increasing the swallowability of the cell collection devices 105.

Figure 22:
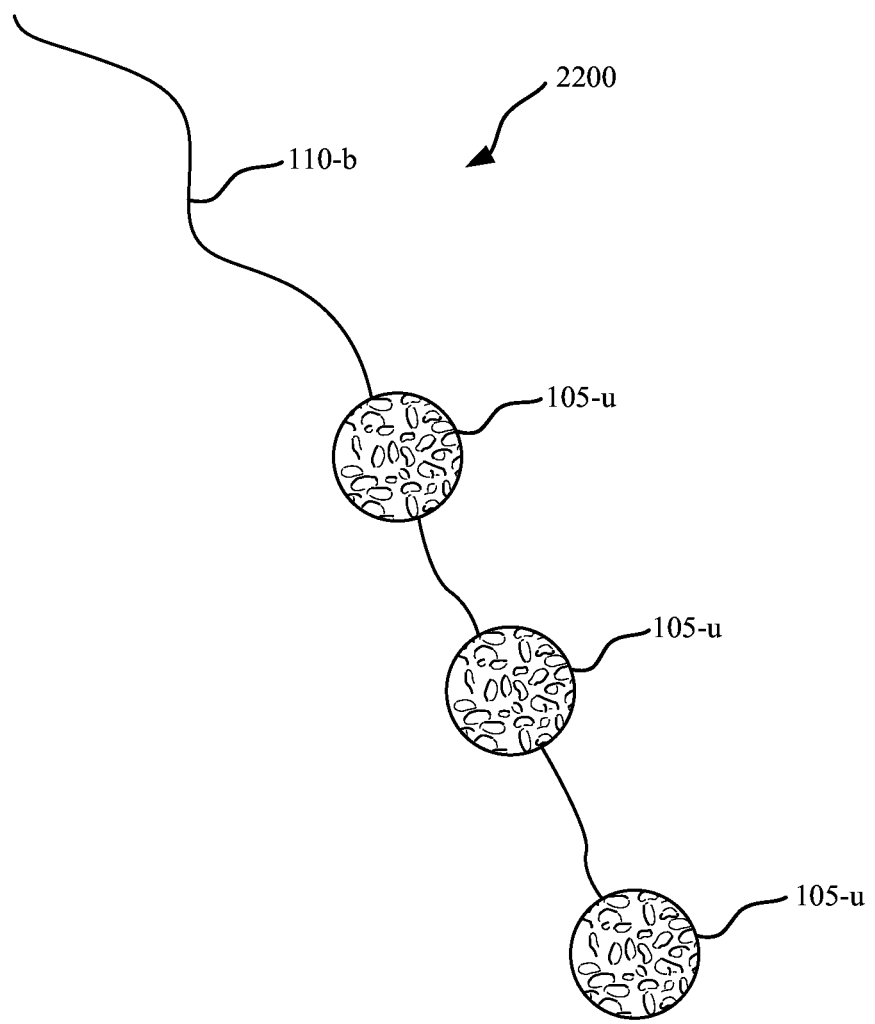
FIG. 22 is an illustration of a cell collection apparatus in accordance with various embodiments.

With reference to FIG. 22, a general system 2200 for collecting cells from a body lumen is shown in accordance with various embodiments. System 2200 may include multiple cell collection devices 105-*u*. Cell collection devices 105-*u* may be examples of any cell collection device 105 described in connection with any of FIGS. 1-21. For example, cell collection device 105-*u* may be an example of a general cell collection device 105 comprising an abrasive material configured to collect cells from a body lumen by scraping a surface of the body lumen as described in connection with FIGS. 1-2. In other embodiments, cell collection device 105-*u* may be an example of any of the cell collection devices comprising multiple distinct regions described in connection with FIGS. 3-9. Additionally or alternatively, cell collection device 105-*u* may be an example of a cell collection device with a tapered geometry as described in connection with any of FIGS. 10-14. Lastly, cell collection device 105-*u* may include one or more expansion elements, either internally or externally, as described in FIGS. 15-21.

System 2200 may also include a retrieval string 110-*b*, which may be an example of retrieval string 110 described in connection with FIGS. 1-2. Cell collection devices 105-*u* may be coupled with retrieval string 110-*b* such that all of the cell collection devices 105-*u* may be retrieved simultaneously. Cell collection devices 105-*u* may be adhered, tied, or otherwise affixed to retrieval string 110-*b*. As shown in FIG. 22, cell collection devices 105-*u* may be coupled with retrieval string 110-*b* in a spaced apart configuration. A spaced apart configuration refers to a configuration where there is a gap between each of cell collection devices 105-*u* such that they do not contact each other when suspended by the retrieval string 110-*b* in open air. In such a configuration, each of cell collection devices 105-*u* may be affixed to a single and continuous retrieval string 110-*b* similar to a string of pearls configuration. In other aspects, each cell collection device 105-*u* is coupled with one another by a distinct and separate portion of retrieval string 110-*b*. The length of retrieval string 110-*b* between each cell collection device 105-*u* may be fixed in some embodiments such that the distance between each of the cell collection devices 105-*u* remains substantially constant while the devices are being withdrawn from a body lumen. However, in other examples, a distance or other spatial relationship between cell collection devices 105-*u* may be adjusted while the cell collection devices 105-*u* are being retrieved from the body lumen.

Moreover, in accordance with some embodiments, cell collection devices 105-*u* may be compressed and encased within one or more capsules 115 described in connection with FIGS. 1-2 and FIG. 26. For example, multiple cell collection devices 105-*u* may be compressed and encased within a single capsule 115. In other embodiments, each of the multiple cell collection devices 105-*u* may be compressed within their own respective capsule 115. Although three cell collection devices 105-*u* are shown in FIG. 22, it may be appreciated that two, four, five, or any other number of cell collection devices 105-*u* may be used to adapt the cell collection apparatus to a particular procedure or body lumen.

Figure 23A:
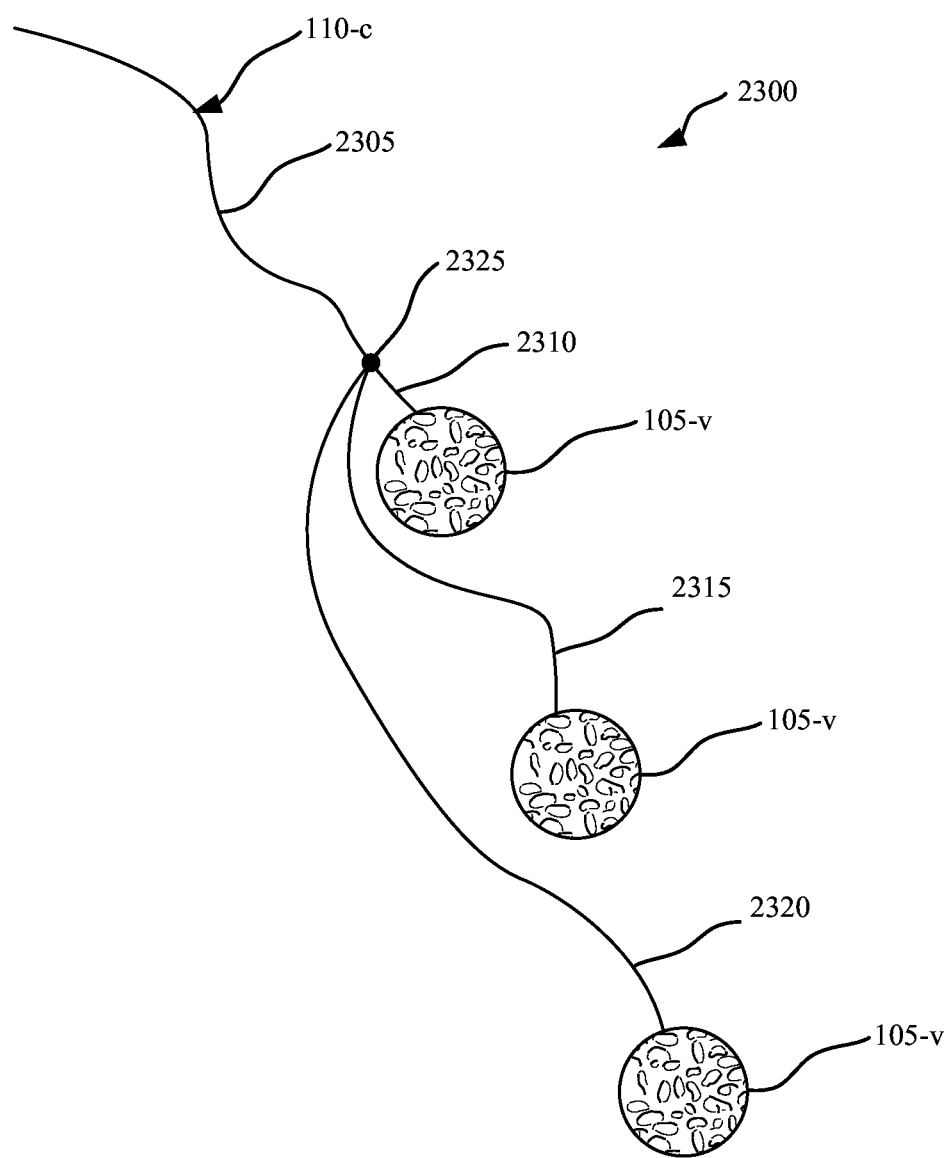
FIG. 23A is an illustration of a cell collection apparatus in a spaced apart configuration in accordance with various embodiments.

With reference to FIG. 23A, a general system 2300 for collecting cells from a body lumen is shown in a spaced apart configuration in accordance with various embodiments. System 2300 may be an example of system 2200 described in connection with FIG. 22. System 2300 may include multiple cell collection devices 105-*v* coupled with a retrieval string 110-*c*. As with system 2200, cell collection devices 105-*v* and retrieval string 110-*c* may be examples of any of the cell collection devices 105 and retrieval strings 110 described in connection with any FIGS. 1-21. Retrieval string 110-*c* may include a main portion 2305 that is proximal to the physician or operator of the cell collection apparatus as the cell collection devices 105-*v* are being retrieved. Each cell collection device 105-*v* may be coupled with main portion 2305 of string 110-*c* by individual connector strings 2310, 2315, and 2320. Individual connector strings 2310, 2315, and 2320 may be made from the same material or exhibit the same mechanical characteristics as main portion 2305. However, as described in more detail below, individual connector strings 2310, 2315, and 2320, may be made from different materials or exhibit different mechanical properties than main portion 2305 and/or than each other. Individual connector strings 2310, 2315, and 2320 may be coupled with main portion 2305 at a junction 2325.

Figure 23B:
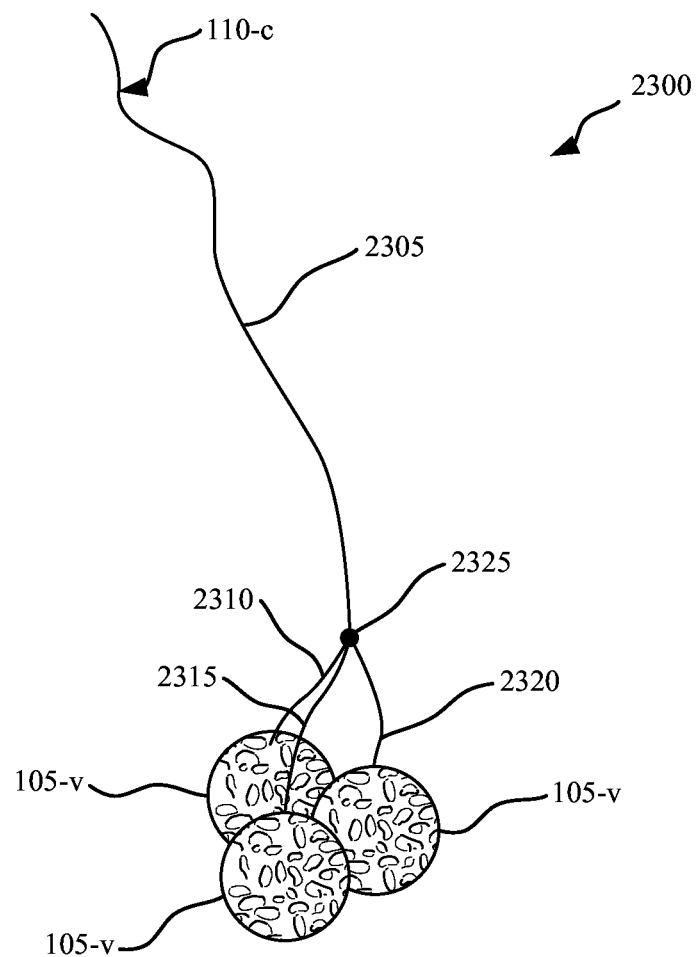
FIG. 23B is an illustration of a cell collection apparatus in a grouped configuration in accordance with various embodiments.

Referring to FIG. 23B, system 2300 is shown with the cell collection devices 105-*v* in a grouped configuration. According to various embodiments, the cell collection devices 105-*v* may be transitioned between a spaced apart configuration (as shown in FIG. 22 or FIG. 23A) and a grouped configuration (as shown in FIG. 23B). A grouped configuration may refer to a configuration where at least two cell collection devices 105-*v* are in contact with each other. For example, cell collection devices 105-*v* may be grouped in a bouquet configuration as shown in FIG. 23B. In some embodiments, junction 2325 is configured to transition the cell collection devices 105-*v* between a spaced apart configuration and a grouped configuration. For example, junction 2325 may facilitate the individual movement of each of the connector strings 2310, 2315, and 2320. Accordingly, to transition from the spaced apart configuration of FIG. 23A to the grouped configuration of FIG. 23B, some or all of the connector strings 2310, 2315, and 2320 may be adjusted such that their lengths are substantially equal. This may be accomplished by shortening connector strings 2320 and 2315 such that their lengths are substantially equal to connector string 2310. Alternatively, connector strings 2310 and 2315 may be lengthened such their lengths are substantially equal to connector string 2320. It may be appreciated that any combination of connector string adjustment may be possible to transition the cell collection devices 105-*v* between a spaced apart configuration and a grouped configuration.

Adjusting the length of connector strings 2310, 2315, and 2320 may be accomplished by several means. In some embodiments, at least one of the connector strings 2310, 2315, 2320 is made from a material with an elastic modulus that differs from the elastic modulus of at least one of the other connector strings. For example, connector strings 2310, 2315, and 2320 may have elastic moduli E1, E2, and E3, respectively such that E1>E2>E3. According to the present example, connector string 2320 will be easier to stretch than connector string 2315, which will be easier to stretch than connector string 2310. Accordingly, as described in more detail below with reference to FIG. 24, as the cell collection devices 105-*v* are being retrieved through the body lumen and experience frictional resistance from the inside surface of the body lumen, connector strings 2310, 2315 and 2320 may each stretch according to their respective elastic moduli such that they form a spaced apart configuration. When the resistance is lessened or removed, connector strings 2315 and 2320 may return to their initial lengths such that the cell collection devices 105-*v* return to a grouped configuration.

Alternatively, in various embodiments, connector strings 2310, 2315, and 2320 may all be substantially non-distensible. In such embodiments, the length of connector strings 2310, 2315, and 2320 may be adjusted relative to each other by letting out and retrieving each of the connector strings 2310, 2315, 2320 through the junction 2325. For example, individual connector strings 2310, 2315, and 2320 may extend from their respective cell collection device 105-*v*, through junction 2325, and all the way until they exit the body lumen proximal to the physician or operator. As such, each of the connector strings 2310, 2315, and 2320 may be individually manipulated. It may be appreciated that such an arrangement would permit a physician or other operator to adjust the distance between each of the cell collection devices 105-*v* by manipulating the lengths of each connector string 2310, 2315, and 2320.

Figure 24:
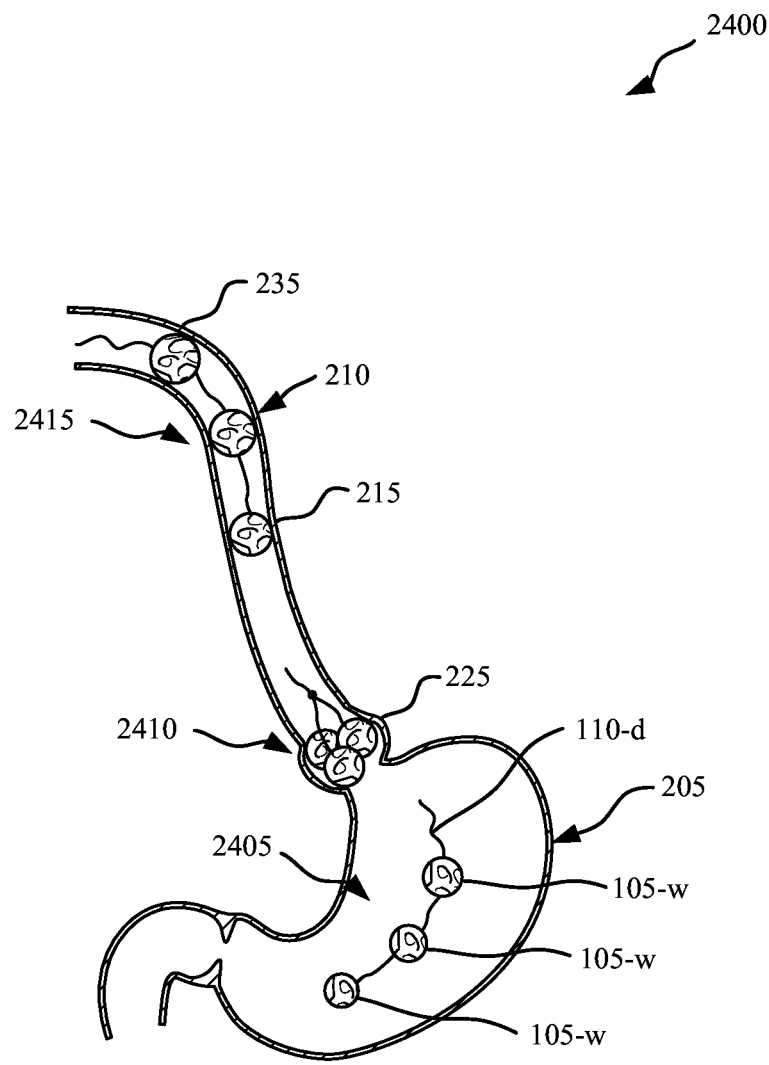
FIG. 24 is an illustration of a cell collection apparatus transitioning between a spaced apart configuration and a grouped configuration while being withdrawn from the upper gastrointestinal tract of a human.

For example, with reference to FIG. 24, a general system 2400 for collecting cells from a body lumen is shown being retrieved from a stomach 205 and up through an esophagus 210. As described in detail with reference to FIG. 2D, the esophagus 210 may include one or more portions 215, 225, 235 with varying shape or size. It may be desirable to collect cells from each of these portions 215, 225, 235 with a single cell collection apparatus. Accordingly, system 2400 may be configured to adapt or adjust according to the local size of the esophagus 210 as it is being withdrawn to collect cells from the various portions 215, 225, 235. System 2400 may be an example of system 2200 or 2300 described in connection with FIGS. 22-23 and may include a retrieval string 110-d coupled with multiple cell collection devices 105-w, which may be examples of any cell collection device 105 described with reference to any of FIGS. 1-21.

The cell collection devices 105-w are shown at three different locations within the upper gastrointestinal tract as the cell collection devices 105-w are being withdrawn to illustrate an exemplary operation of cell collection system 2400. The cell collection devices 105-w are shown initially at 2405 within the stomach 205 in a spaced apart configuration. The cell collection devices 105-w may be configured to initially be in a spaced apart configuration after being released from one or more dissolvable capsules 115 (not shown). As the cell collection devices 105-w are being retrieved out of the stomach 205 and into the esophagus 210, they may be transitioned into a grouped configuration as shown at 2410. The cell collection devices 105-w may transition from a spaced apart configuration to a grouped configuration by any means described in connection with FIGS. 23A-23B. Grouping the cell collection devices 105-w effectively forms a compound cell collection device 105-w that has a larger diametric dimension than any of cell collection devices 105-w individually, thereby facilitating the collection of cells from an enlarged portion 225, which may not otherwise be feasible if the cell collection devices 105-w were maintained in a spaced apart configuration.

Furthermore, as shown at 2415, cell collection devices 105-w may be transitioned back into a spaced apart configuration as the cell collection devices 105-w are being withdrawn past portions 215 and 235 of the esophagus 210. Transitioning the cell collection devices 105-w back into a spaced apart configuration may increase the ease with which the cell collection devices 105-w are withdrawn from the throat and out of the mouth of a patient. It may be appreciated that the operation of system 2400 described in connection with FIG. 24 is but one example of how system 2400 may be used to collect cells from a body lumen. For example, the cell collection devices 105-w may be transitioned between a spaced apart configuration and grouped configuration more or less times than described in connection with FIG. 24. In general, system 2400 may be adapted for use in a wide variety of procedures with a variety of gastrointestinal physiologies.

Figure 25:
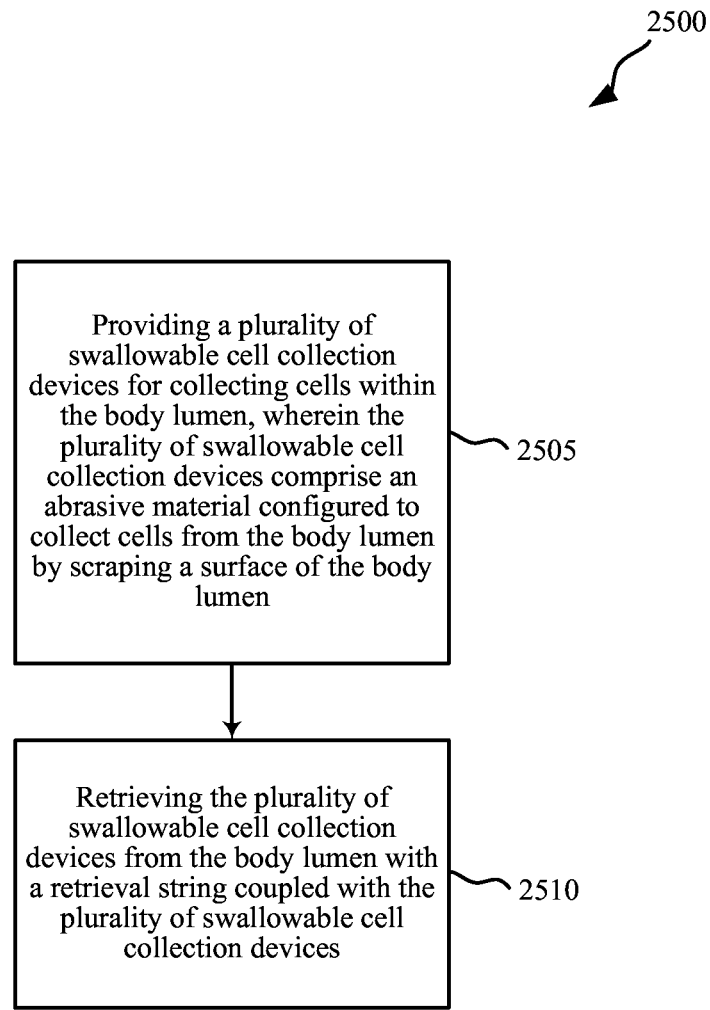
FIG. 25 is a flow chart of a method of collecting cells from a body lumen in accordance with various embodiments.

Turning to FIG. 25, a method 2500 for collecting cells from a body lumen is described in accordance with various embodiments. At block 2505, the method may include providing a plurality of swallowable cell collection devices 105 for collecting cells within the body lumen, wherein the plurality of swallowable cell collection devices 105 comprise an abrasive material configured to collect cells from the body lumen by scraping a surface of the body lumen. Furthermore, at block 2510, the method may include retrieving the plurality of swallowable cell collection devices 105 from the body lumen with a retrieval string 110 coupled with the plurality of swallowable cell collection devices 105. Method 2500 may be implemented with any of the cell collection apparatuses or systems described in connection with FIGS. 22-24.

In some embodiments, retrieving the plurality of swallowable cell collection devices 105 described at block 2510 may comprise adjusting a spatial relationship between at least one of the swallowable cell collection devices 105 with respect to at least one other swallowable cell collection device 105. In certain aspects, adjusting a spatial relationship may comprise transitioning the plurality of swallowable cell collection devices 105 between a grouped configuration and a spaced apart configuration. The adjusting a spatial relationship and transiting between spaced apart and grouped configurations may be implemented by any of the means and apparatuses described in connection with FIGS. 23-24. In some examples, a diametric dimension of the plurality of swallowable cell collection devices 105 in the grouped configuration is greater than a diametric dimension of any of the swallowable cell collection devices 105 individually. Furthermore, as described in FIG. 24, the cell collection devices 105 may be transitioned into a group configuration when the devices 105 are being withdrawn past a portion of the body lumen (such as portion 225) where a diametric dimension of the body lumen exceeds the diametric dimension of any of the swallowable cell collection devices 105 individually.

As described in connection with FIG. 1B, a system for collecting cells from a body lumen may include a capsule 115 configured to releasably retain a cell collection device 105. With reference to FIG. 26A, a capsule 115-b is shown in accordance with various embodiments. Capsule 115-b may be an example of capsule 115 described in connection with any of FIGS. 1-2. Accordingly, capsule 115-b may be swallowable and dissolvable and be configured to retain a cell collection device 105 in a compressed configuration. Capsule 115-b may have a substantially smooth outer surface and may have a substantially uniform wall thickness. However, in certain circumstances a capsule 115 such as capsule 115-b may take an undesirably long time to dissolve once it is within the body lumen. Additionally, it is difficult to predict or control how capsule 115-b will dissolve and release the compressed cell collection device 105 due to the uniform nature of the capsule walls. Therefore, according to various embodiments, a capsule 115 may include one or more scoring features that are configured to mechanically weaken the walls of a capsule 115. Mechanically weakening the capsule 115 may reduce the dissolution time as compared to a smooth-walled capsule. Moreover, as described in more detail below, the one or more scoring features may be arranged and configured to control how the capsule 115 dissolves and fractures, thereby controlling the orientation of a cell collection device 105 with respect to the capsule 115 when it is released from the capsule 115.

For example, referring to FIG. 26B, a capsule 115-c with one or more scoring features is shown according to various embodiments. Capsule 115-c may be an example of any capsule 115 described with reference to FIGS. 1-2 and 26A. Accordingly, capsule 115-c may be configured to encase a cell collection device 105 in a compressed configuration. In some embodiments, the encased cell collection device 105 may comprise an abrasive and substantially non-absorbent material configured to collect cells from the body lumen by scraping a surface of the body lumen. As shown in FIG. 26B, the one or more scoring features may include one or more slits 2610. Slits 2610 may pierce all the way through the wall of capsule 115-c or they may merely score the surface of capsule 115-c. In some embodiments, slits 2610 are arranged longitudinally along a longitudinal axis of capsule 115-c, and are evenly spaced circumferentially around the longitudinal axis. Slits 2610 may extend along the entire length of the capsule 115-c or, in some examples, slits 2610 may extend along a partial length of capsule 115-c. Moreover, slits 2610 may extend around one or both ends of capsule 115-c from one side of the capsule 115-c to the opposite side.

In yet other embodiments, slits 2610 may be arranged in a latitudinal orientation, rather than the longitudinal orientation shown in FIG. 26B. In some aspects, one or more slits 2610 may be angled with respect to the longitudinal axis of the capsule 115-c or the slits 2610 may be oriented in a spiraled configuration along the longitudinal axis. It may be appreciated that slits 2610 may be arranged in any number of orientations and configurations depending on the particular application.

In accordance with various embodiments, the slits 2610 may be configured to control the orientation of the cell collection device 105 with respect to the capsule 115-c when the cell collection device 105 is released from the capsule 115-c. By manipulating the orientation, size, location, and density of the slits 2610, the location on the capsule 115-c where the capsule wall first dissolves or fractures enough to allow the cell collection device 105 to be released and expand may be controlled. For example, if slits 2610 are arranged exclusively near one end of the capsule 115-c, it may be appreciated that this end of the capsule 115-c will likely dissolve before the other end of the capsule 115-c, thereby releasing the cell collection device 105 from the end with the slits 2610. In another example, one or more slits 2610 may be arranged circumferentially near the middle of capsule 115-c such that the capsule wall near the middle of the capsule 115-c will fracture first, resulting in capsule 115-c breaking into two nearly equal halves or hemispheres.

Additionally or alternatively, as shown in FIG. 26C, the one or more scoring features may include one or more indentations 2615 arranged on a surface of a capsule 115-d. Capsule 115-d may be an example of any of the capsules 115 described in connection with FIGS. 1-2 and 26A-26B. Indentations 2615 may be configured to weaken the wall of capsule 115-d without piercing all the way through the walls. According to various embodiments, indentations 2615 may be arranged longitudinally along a longitudinal axis of capsule 115-d. In some examples, the indentations 2615 may be arranged perpendicular to the longitudinal axis of capsule 115-d, or at some angle to the longitudinal axis. It may be appreciated that the indentations 2615 may be arranged or configured in any orientation or combination of orientations similar to the slits 2610 described with reference to FIG. 26B. Indentations 2615 may be arranged and configured to control the orientation of the cell collection device 105 with respect to the capsule 115-d when the cell collection device 105 is released from the capsule 115-d. Alternatively, indentations 2615 may be arranged randomly throughout the capsule 115-d for the purposes of generally weakening the wall of capsule 115-d to reduce the dissolution time as compared to a smooth-walled capsule like capsule 115-b described with reference to FIG. 26A. In some embodiments, indentations 2615 may be generally circular, such as the ones shown in FIG. 26C, or they may be triangular, oval, or star-shaped. Moreover, indentations 2615 may all be the same size, or may alternatively be comprised of various sizes.

Turning to FIG. 26D, a capsule 115-e is shown with one or more scoring features in the form of a plurality of fenestrations 2620 in accordance with various embodiments. Capsule 115-e may be an example of a capsule 115 described with reference to any of FIGS. 1-2 and 26A-26C. Fenestrations 2620 differ from indentations 2615 in that fenestrations 2620 pierce all the way through the walls of capsule 115-e, allowing liquid to travel through the capsule walls. Accordingly, fenestrations 2620 may permit liquid and other contents of a body lumen to dissolve capsule 115-e from both the outside and inside surfaces of the capsule walls simultaneously, which may reduce the dissolution time of capsule 115-e as compared to a smooth-walled capsule 115-b. As shown in FIG. 26D, fenestrations 2620 may be circularly-shaped and may be substantially evenly distributed around the surface of capsule 115-e. Additionally, fenestrations 2620 may include various shapes including but not limited to squares, polygons and ovals. It may be appreciated that fenestrations 2620 may be arranged in any pattern or grouping similar to slits 2610 and indentations 2615 as described with reference to FIGS. 26B and 26C, respectively. Moreover, the size, location, orientation, and density of fenestrations 2620 may be configured to control the orientation of a cell collection device 105 when it is released from capsule 115-e.

According to various embodiments, a capsule 115 may be comprised of more than one material. For example, referring to FIG. 26E, a capsule 115-f is shown in accordance with various embodiments. Capsule 115-f may be an example of any capsule 115 described in connection with FIGS. 1-2 and 26A-26D. Capsule 115-f may include a first region 2625 made from a first material and a second region 2630 made from a second material that is different than the first material. The material of region 2625 may be chosen or configured to dissolve at a faster rate in the presence of liquid, heat, acidity or the general environment of a body lumen as compared to the material of region 2630. Accordingly, the dissolution time of capsule 115-f may be determined and controlled by the material chosen for region 2625, while the remaining material of region 2630 may be chosen for other characteristics such as mechanical strength, cost, swallowability, or ease of manufacturing.

As shown in FIG. 26E, region 2625 may form a band around the circumference of capsule 115-f near the middle of capsule 115-f. In an alternative embodiment, region 2625 may run parallel to the longitudinal axis of capsule 115-f. However, it may be appreciated that there may be any number of regions made from any number of materials, and these portions may take on a variety of shapes, sizes, and orientations as required by a particular application.

Figure 27:
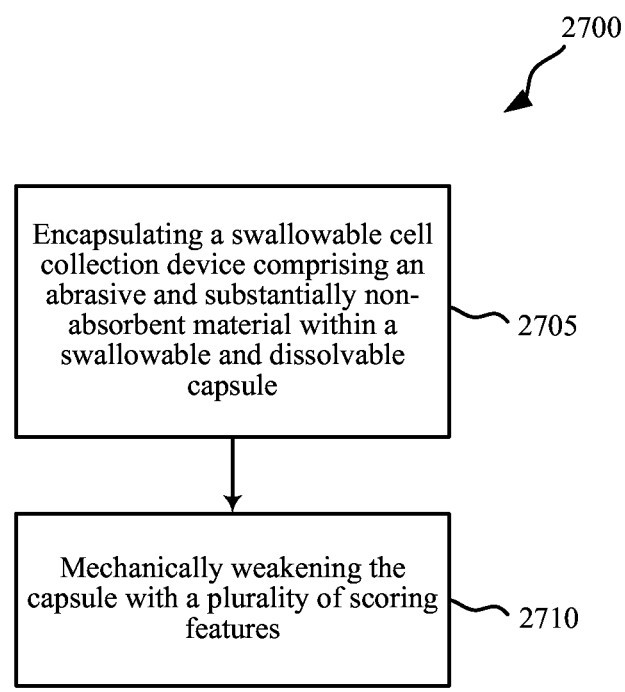
FIG. 27 is a flow chart of a method of collecting cells from a body lumen in accordance with various embodiments.

With reference to FIG. 27, a method 2700 for manufacturing an apparatus for collecting cells from a body lumen in accordance with various embodiments is described. At block 2705, the method 2700 may include encapsulating a swallowable cell collection device 105 comprising an abrasive and substantially non-absorbent material within a swallowable and dissolvable capsule 115. The cell collection device 105 may be an example of any of the cell collection devices 105 described in connection with any of FIGS. 1-24. Moreover, the dissolvable capsule 115 may be an example of any of the dissolvable capsules 115 described in connection with any of FIGS. 1-2 and 26. Encapsulating a cell collection device 105 may include forming a capsule 115 around a compressed cell collection device 105. Alternatively, encapsulating a cell collection device 105 may include compressing and stuffing a cell collection device 105 into a preformed capsule 115.

Method 2700 may also include, at block 2710, mechanically weakening the capsule with a plurality of scoring features. In some embodiments, the scoring features may comprise one or more fenestrations 2620 as described in connection with FIG. 26D. As described with reference to FIG. 26B, the scoring features may comprise one or more slits 2610. In certain aspects, as described in connection with FIG. 26C, mechanically weakening the capsule 115 may include indenting the capsule 115 with one or more indentations 2615. Moreover, method 2700 may include mechanically weakening the capsule 115 with a plurality of scoring features that are configured to control the orientation of the cell collection device 105 with respect to the capsule 115 when the cell collection device 105 is released from the capsule 115, as described with reference to FIGS. 26B-26D.

As described with reference to FIGS. 1-2, a cell collection device 105 may be compressed and encased within a capsule 115 that releases the cell collection device 105 from the compressed configuration once the capsule 115 is within the body lumen. For various reasons, the cell collection device 105 may be released from the capsule 115 at an undesirable location within the body lumen, or the cell collection device 105 may be released at an undesirable time during the cell collection procedure. For example, the capsule 115 may dissolve prematurely in the patient's esophagus 210 when the cell collection device 105 is being swallowed, which may require the procedure to be repeated thereby increasing discomfort to the patient and the cost of the procedure. In other circumstances, the capsule 115 may take an undesirably long time to dissolve once properly placed within the body lumen, which again increases the discomfort to the patient. Accordingly, it may be desirable to more precisely control the time and manner in which the cell collection device 105 is released from the capsule 115.

According to various embodiments of the present invention, the manner and timing of the release of the cell collection device 105 from the capsule 115 may be controlled. Controlling the release of the cell collection device 105 ensures that the cell collection device 105 is being released in the proper location within the body lumen and within a desirable amount of time. In some embodiments, a capsule 115 is configured to encase a cell collection device 105 in a compressed configuration until the activation of one or more active triggers that control the release of the cell collection device 105 from the capsule 115. An active trigger may be any trigger or event that is initiated or actively controlled by an operator or user of a cell collection device 105. An active trigger may be applied to a capsule 115 either directly or indirectly. For example an active trigger may be electrical, chemical, or thermal in nature and may be applied directly to the capsule 115 or may be applied to the surroundings or environment of the capsule 115 within the body lumen. In contrast, a passive trigger is one that is not directly controlled or initiated by the operator or user of the cell collection device 105. For example, simply placing a capsule 115 containing a cell collection device 105 within a body lumen and allowing the capsule 115 to dissolve naturally based on the inherent environment of the body lumen may be considered a passive dissolution and release of the cell collection device 105 from the capsule 115.

Figure 28:
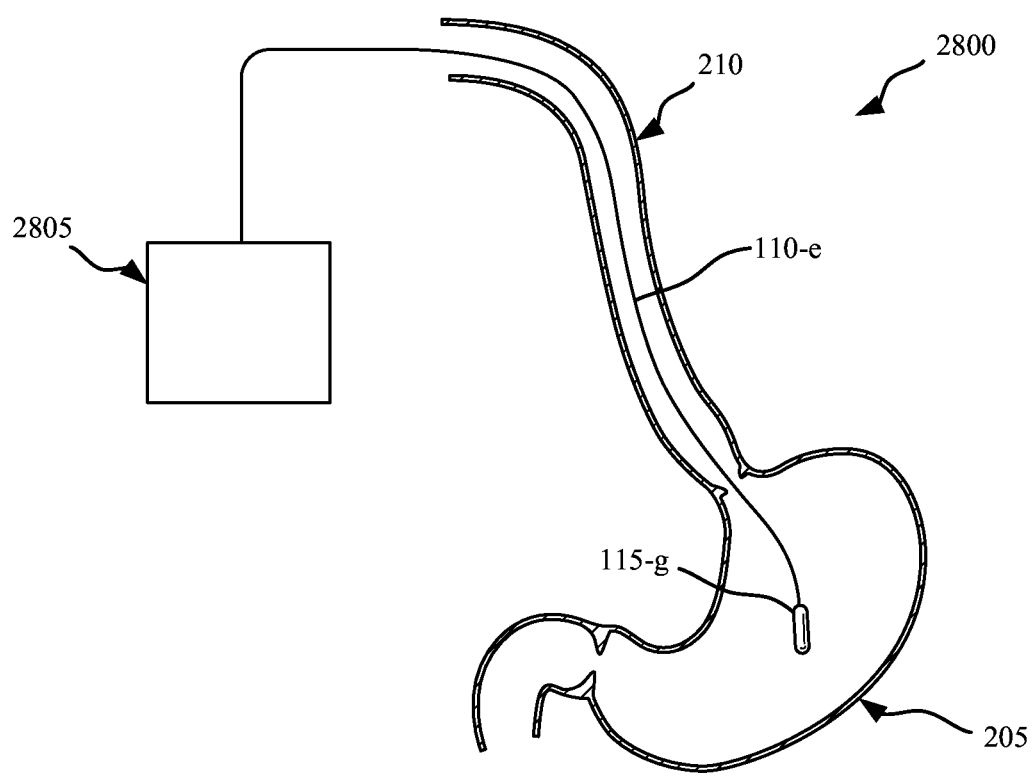
FIG. 28 is an illustration of a cell collection apparatus within the upper gastrointestinal tract of a human in accordance with various embodiments.

With reference to FIG. 28, a general system 2800 for collecting cells from a body lumen is shown according to various embodiments. System 2800 may be an example of any of systems 100, 200, 2200, 2300, or 2400 described in connection with FIGS. 1-2, and 22-24. System 2800 may include a capsule 115-g coupled with a retrieval string 110-e, which may be an example of a capsule 115 and retrieval string 110 described in connection with any of the FIGS. 1-26. Accordingly, capsule 115-g may be configured to releasably retain a cell collection device 105 (not shown), which may be any cell collection device 105 described with reference to any of FIGS. 1-24. In some embodiments, capsule 115-g is configured to releasably retain a cell collection device 105 in a compressed configuration until the activation of one or more active triggers that control the release of the cell collection device 105 from capsule 115-g.

As shown in FIG. 28, system 2800 may include a generator 2805 that is configured to apply one or more active triggers to capsule 115-g via the retrieval string 110-e. In some embodiments, generator 2805 may apply an electrical current to the capsule 115-g through the retrieval string 110-e. In such embodiments, the retrieval string 110-e may be made from or include a conductive material. In some embodiments, capsule 115-g may be configured to dissolve or otherwise release a cell collection device 105 in response to the application of the electrical current active trigger from the generator 2805. For example, capsule 115-g may be configured to dissolve due to an increase in heat from the application of the electrical current from generator 2805. Capsule 115-g may be configured to dissolve due to the breakdown of bonds that form the material of the capsule 115-g.

Figure 29:
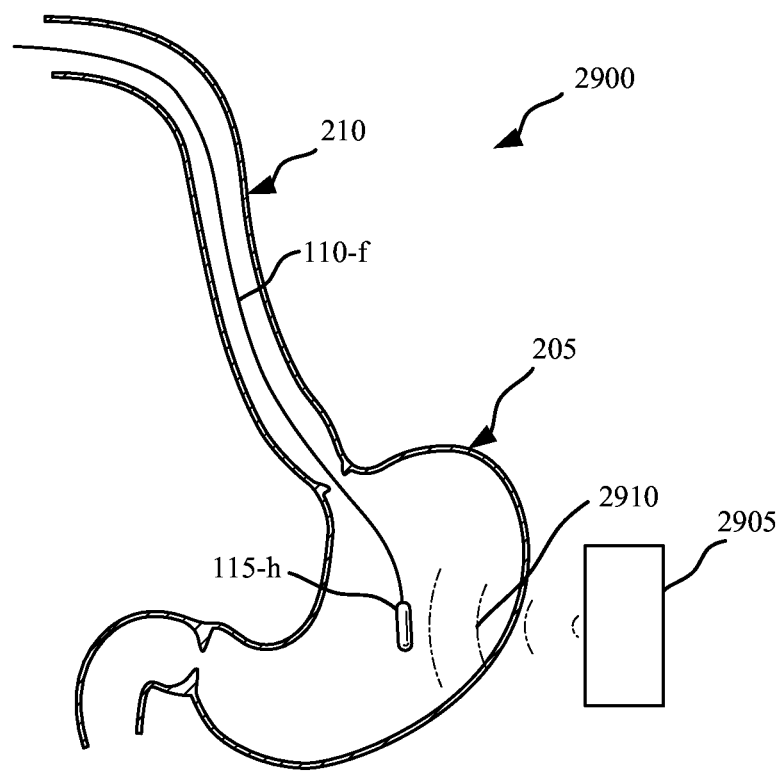
FIG. 29 is an illustration of a cell collection apparatus within the upper gastrointestinal tract of a human in accordance with various embodiments.

Turning to FIG. 29, a general system 2900 for collecting cells from a body lumen is shown according to various embodiments. System 2900 may be an example of any of systems 100, 200, 2200, 2300, 2400 or 2800 described in connection with FIGS. 1-2, 22-24, and 28. System 2900 may include a capsule 115-h coupled with a retrieval string 110-f, which may be examples of a capsule 115 and retrieval string 110 as described in any of FIGS. 1-28. According to various embodiments, capsule 115-h may be configured to releasably retain a cell collection device 105 (not shown) in a compressed configuration until the activation of one or more active triggers that control the release of the cell collection device 105. For example, system 2900 may include a generator 2905 configured to indirectly apply one or more active triggers to the capsule 115-h. In some embodiments, the active trigger may be an electromagnetic wave 2910 that is emitted from generator 2905. Electromagnetic wave 2910 may interact either directly or indirectly to dissolve or otherwise act to release the cell collection device 105 from the capsule 115-h. For example, the electromagnetic wave 2910 may heat up the capsule 115-h directly or may heat up the environment surrounding capsule 115-h thereby initiating the dissolution of capsule 115-h. Capsule 115-h may be configured to dissolve due to the breakdown of bonds that form the material of capsule 115-h. Additionally or alternatively, capsule 115-h may dissolve due to the electromagnetic wave 2910 increasing the osmotic susceptibility of the capsule material, and/or increasing the rate of osmotic uptake by the material.

Moreover, a capsule 115 may be configured to dissolve in response to various other active triggers. For example, capsule 115 may be configured to dissolve in the presence of a particular substance or solution that is swallowed by the patient or otherwise introduced into the body lumen where the capsule 115 is to dissolve. In certain aspects, the capsule 115 is configured to dissolve by chemically reacting with the solution. Additionally or alternatively, the solution may be heated above the natural temperature of the body lumen before being swallowed, thereby heating up the capsule 115.

In yet other embodiments, the dissolvable capsule 115 may be configured to dissolve in response to the acidic liquids of the stomach. For example, capsule 115 may comprise one or more pH-sensitive polymers, which may be configured to be reactive to the changes in the pH of the surrounding medium by directly degrading certain elements within the polymeric backbone. In some embodiments, capsule 115 may comprise ethyl acrylic acid (EAA), which may degrade and dissolve in the acidic conditions of the stomach.

In other examples, capsule 115 may comprise one or more materials that are configured to increase in size (swell) or collapse based on the pH of the surrounding environment. In accordance with certain embodiments, capsule 115 may comprise a material, such as chitosan, with one or more pH-sensitive acidic groups that swell in an acidic pH liquid. The swelling of such a material in response to the acid pH liquid may cause capsule 115 to break apart or otherwise dissolve in the presence of stomach acids. Another example of a pH-sensitive material is polyacrylic acid, which includes one or more pH-sensitive acidic groups that swell in basic pH liquid.

Moreover, in certain embodiments, capsule 115 may comprise a combination of dissimilar metals and alloys. It may be appreciated that dissimilar metals have different electrode potentials, and when two or more come into contact in an electrolyte, one metal acts as anode and the other as cathode. In particular, the electrical potential difference between the dissimilar metals is the driving force for an accelerated attack on the anode member of the galvanic couple. Accordingly, the anode metal dissolves into the electrolyte, and deposit collects on the cathodic metal.

Figure 30A:
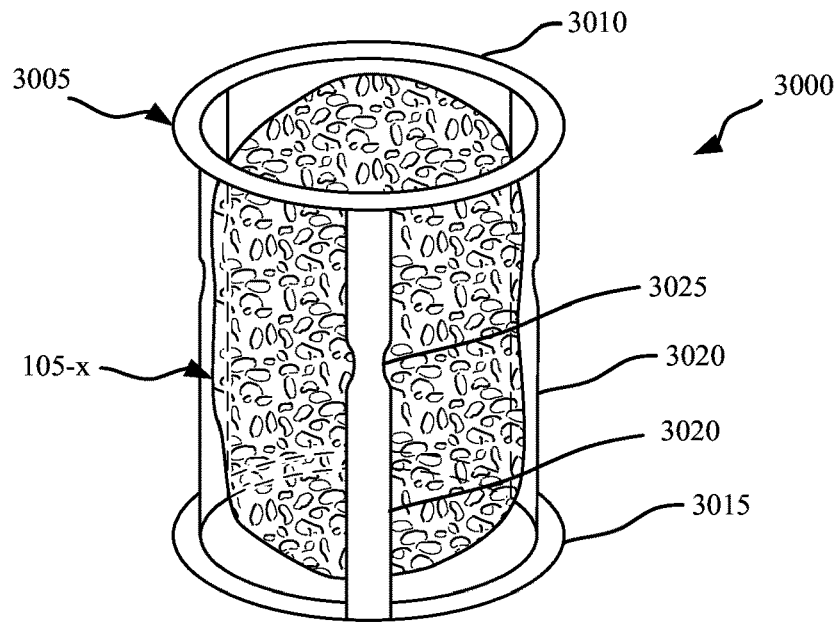
FIG. 30A is an illustration of a cell collection apparatus in accordance with various embodiments.

With reference to FIG. 30A, a system 3000 for collecting cells from a body lumen is shown according to various embodiments. System 3000 may include a cell collection device 105-x that is compressed and contained within a cage 3005. Cage 3005 may be similar to a capsule 115 described in connection with FIGS. 1-2 in that cage 3005 may be swallowable and may be configured to releasably retain a cell collection device 105-x. Cage 3005 may include multiple pillars 3020 that connect upper portion 3010 to lower portion 3015. Although three pillars 3020 are shown in FIG. 30A, it may be appreciated that any number of pillars 3020 may be used. Furthermore, although top portion 3010 and bottom portion 3015 are shown as rings, in some embodiments one or both portions 3010, 3015 are solid disks. According to various embodiments, pillars 3020 may include one or more notches 3025 or any other feature that reduces the local cross section of pillar 3020.

Figure 30B:
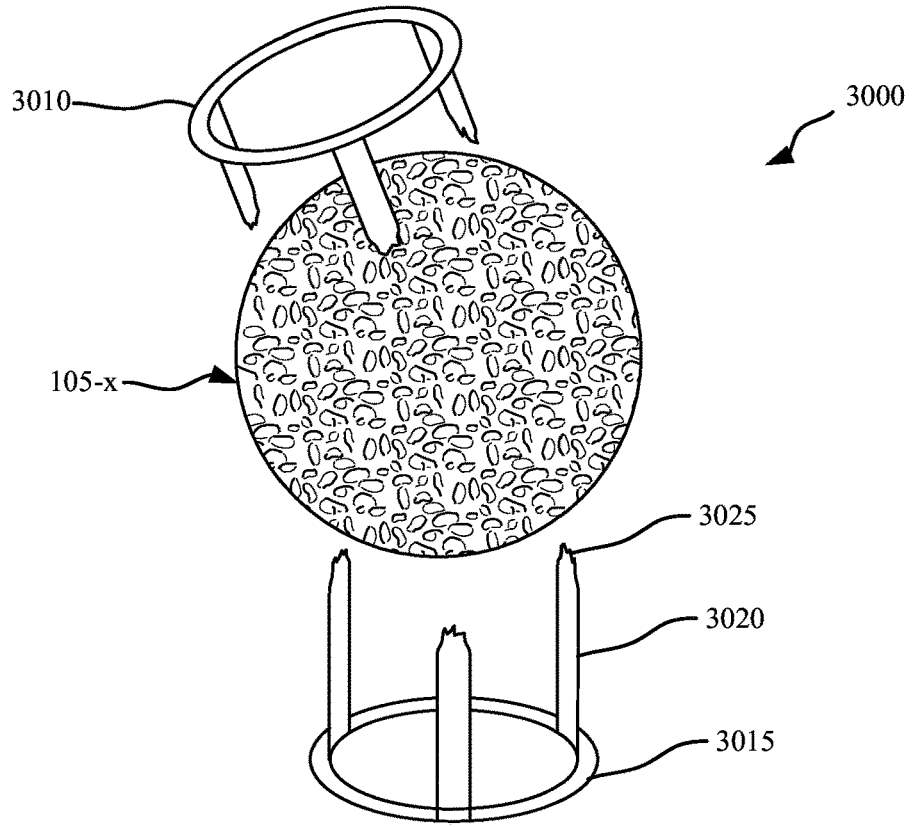
FIG. 30B is an illustration of a cell collection apparatus in accordance with various embodiments.

With reference to FIG. 30B, cage 3005 is shown releasing cell collection device 105-x from the compressed configuration. The dissolution or fracture of cage 3005 and subsequent release of cell collection device 105-x may have been controlled by an active trigger as described in connection with any of FIGS. 28-29. For example, cage 3005 may have been heated by the application of a direct or indirect electrical current from a generator such as generator 2805 or 2905. In other embodiments, cage 3005 may have been heated by the introduction of a heated liquid to the body lumen. Moreover, cage 3005 may have dissolved or fractured in response to a solution or substance swallowed or otherwise introduced into the body lumen that was configured to chemically react with and dissolve cage 3005. It may be appreciated that regardless of the active trigger used, the pillars 3020 of cage 3005 will likely fracture near notch 3025 due to the reduced cross section of pillar 3020 in that area.

Figure 31:
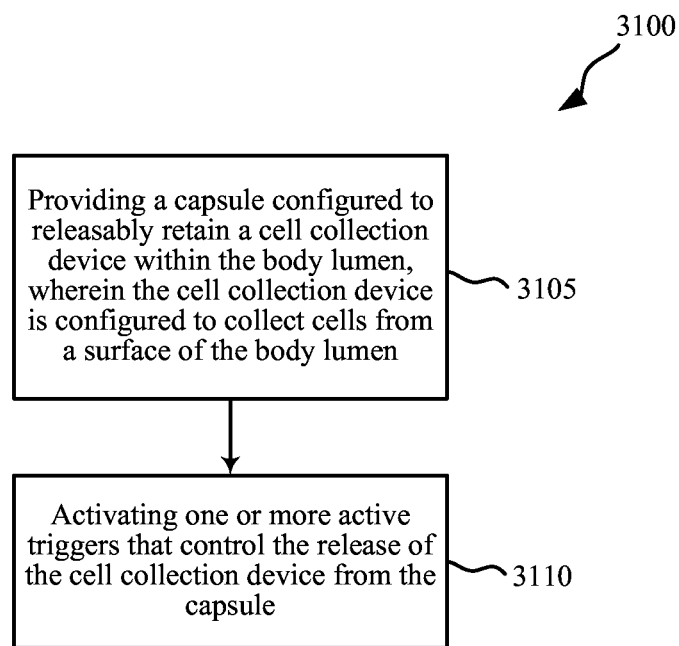
FIG. 31 is a flow chart of a method of collecting cells from a body lumen in accordance with various embodiments.

Turning to FIG. 31, a method 3100 of collecting cells from a body lumen is described in accordance with various embodiments. Method 3100 may include, at block 3105, providing a capsule 115 configured to releasably retain a cell collection device 105 within the body lumen, wherein the cell collection device 105 is configured to collect cells from a surface of the body lumen. The cell collection device 105 and capsule 115 may be examples of any of the cell collection devices 105 and capsules 115 described with reference to any of FIGS. 1-30. Method 3100 may further include, at block 3110, activating one or more active triggers that control the release of the cell collection device 105 from the capsule 115.

Activating the one or more active triggers may include applying an electrical current to the capsule 115, via a retrieval string 110, as described with reference to FIG. 28. In some aspects, the electrical current may be applied indirectly through an electromagnetic field 2910, as described in FIG. 29. In yet other embodiments, applying the one or more active triggers may include swallowing or otherwise introducing a liquid solution to the capsule 115. As described previously, the liquid solution may either chemically or thermally interact with and dissolve the capsule 115 to release the cell collection device 105.

The previous description of the disclosure is provided to enable a person skilled in the art to make or use the disclosure. Various modifications to the disclosure will be readily apparent to those skilled in the art, and the generic principles defined herein may be applied to other variations without departing from the spirit or scope of the disclosure. Throughout this disclosure the term "example" or "exemplary" indicates an example or instance and does not imply or require any preference for the noted example. Thus, the disclosure is not to be limited to the examples and designs described herein but is to be accorded the widest scope consistent with the principles and novel features disclosed herein.

The invention claimed is:

1. An apparatus for collecting cells from a body lumen comprising:
    an abrasive material comprising a plurality of voids and configured to, collect cells from the body lumen and store the cells on a surface of the abrasive material by scraping a surface of the body lumen, wherein:
    the abrasive material, in an uncompressed state, forms a three-dimensional shape having a longitudinal axis, a first end having a first diametric dimension, and a second end having a second diametric dimension that is smaller than the first diametric dimension,
    a cross-section of the three-dimensional shape taken orthogonal to the longitudinal axis at the first end comprises an outer diameter equal to the first diametric dimension and an inner diameter equal to a diameter of a cavity of the three-dimensional shape, wherein the abrasive material having the cavity is configured to be compressed into a swallowable capsule; and
    the first end exerts a first pressure on the surface of the body lumen greater than a second pressure exerted on the surface of the body lumen by the second end, the first pressure greater than the second pressure based at least in part on the second end having a second diametric dimension that is smaller than the first diametric dimension, the first end configured to collect a different type of cells from the surface of the body lumen and store the different type of cells on the surface of the abrasive material than the second end based at least in part on the first pressure being greater than the second pressure.

2. The apparatus of claim 1, wherein the apparatus is shaped as a conical frustum.

3. The apparatus of claim 2, wherein the cavity is shaped as a conical frustum.

4. The apparatus of claim 1, wherein the apparatus is conically shaped.

5. The apparatus of claim 4, wherein the cavity is conically shaped.

6. The apparatus of claim 1, wherein the apparatus is shaped as a paraboloid.

7. The apparatus of claim 6, wherein the cavity is shaped as a paraboloid.

8. The apparatus of claim 1, wherein the cell, collection device is substantially cylindrically shaped.

9. The apparatus of claim 8, wherein the cell, collection device comprises a plurality of fins.

10. The apparatus of claim 1, further comprising a retrieval string coupled with the cell, collection device.

11. The apparatus of claim 10, further comprising a cavity extending from the first end towards the second end, wherein the retrieval string extends through the first end of the cell, collection device.

12. The apparatus of claim 1, wherein the swallowable capsule is a dissolvable capsule configured to releasably retain the apparatus.

* * * * *